(12) United States Patent
Yoshida et al.

(10) Patent No.: US 11,147,526 B2
(45) Date of Patent: Oct. 19, 2021

(54) X-RAY IMAGING APPARATUS

(71) Applicant: Shimadzu Corporation, Kyoto (JP)

(72) Inventors: Takanori Yoshida, Kyoto (JP); Shohei Okubo, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/920,174

(22) Filed: Jul. 2, 2020

(65) Prior Publication Data

US 2021/0077044 A1 Mar. 18, 2021

(30) Foreign Application Priority Data

Sep. 17, 2019 (JP) .............................. JP2019-168740

(51) Int. Cl.
*A61B 6/00* (2006.01)
*A61B 6/04* (2006.01)

(52) U.S. Cl.
CPC ............ *A61B 6/463* (2013.01); *A61B 6/0407* (2013.01); *A61B 6/0487* (2020.08); *A61B 6/4476* (2013.01); *A61B 6/464* (2013.01); *A61B 6/503* (2013.01); *A61B 6/54* (2013.01)

(58) Field of Classification Search
CPC ..... A61B 6/463; A61B 6/0407; A61B 6/0487; A61B 6/503; A61B 6/54; A61B 6/4476; A61B 6/4405; A61B 6/4417; A61B 6/5211; A61B 6/5294; A61B 6/461; A61B 6/52; A61B 6/464; A61B 6/465
See application file for complete search history.

(56) References Cited

U.S. PATENT DOCUMENTS

2011/0317815 A1 12/2011 Bernhardt et al.
2016/0151031 A1* 6/2016 Watanabe ............ A61B 6/5294
378/98.5

* cited by examiner

*Primary Examiner* — Don K Wong
(74) *Attorney, Agent, or Firm* — Muir Patent Law, PLLC

(57) ABSTRACT

An X-ray imaging apparatus includes a moving unit for changing an irradiation position which is a position of a subject to be irradiated with X-rays by moving at least one of an imaging unit for emitting X-rays to a subject and a top board, and a control unit for performing control for displaying on a first display unit a two-dimensional virtual plane image which is a two-dimensional image in which an image indicating the skin dose for each of a plurality of irradiation positions and a scale image indicating at least one of the distance and the angle with respect to a reference position are superimposed on a virtual plane.

13 Claims, 9 Drawing Sheets

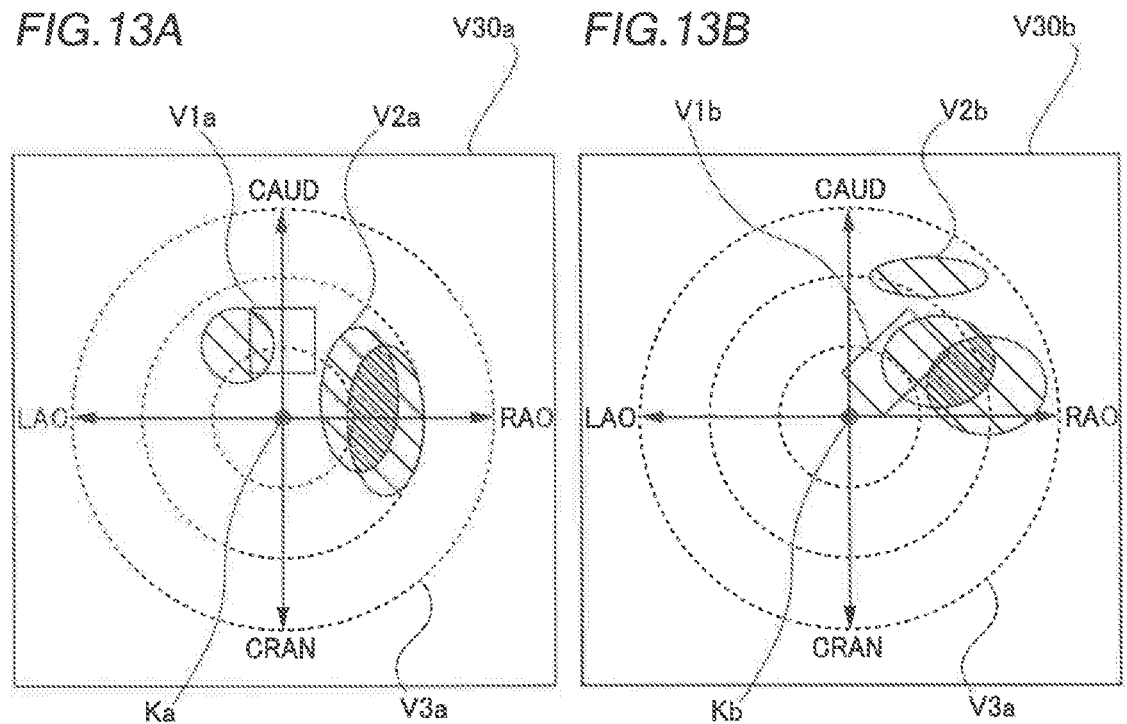
FIG. 13A
FIG. 13B
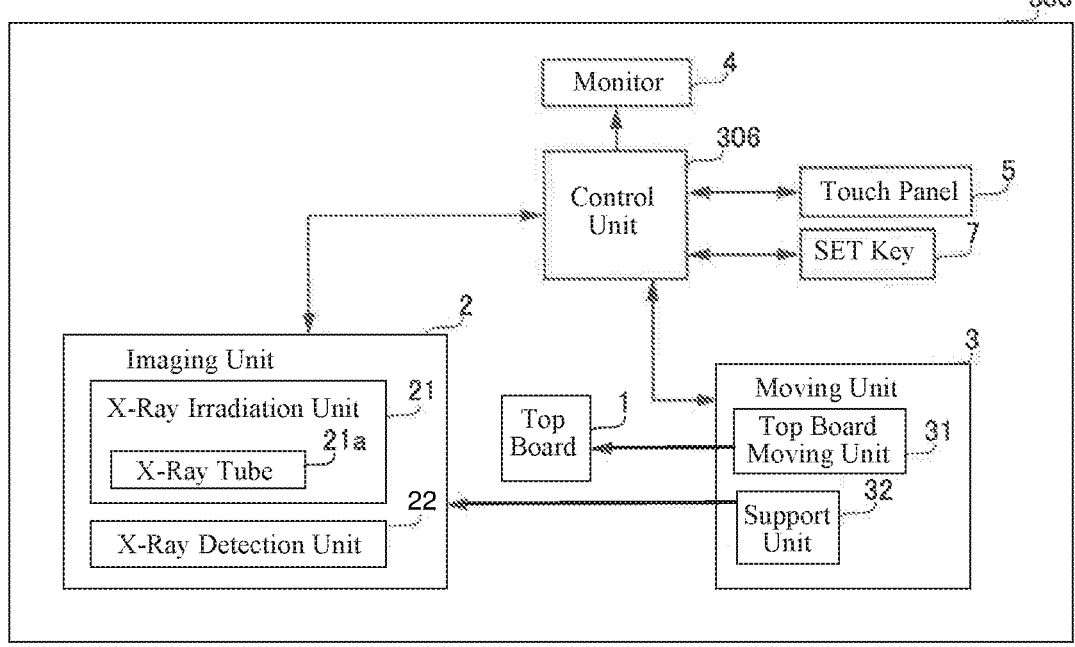
FIG. 14

X-RAY IMAGING APPARATUS

CROSS-REFERENCE TO RELATED APPLICATIONS

The priority application number JP2019-168740, entitled "X-ray imaging apparatus", filed on Sep. 17, 2019, and invented by Takanori Yoshida and Shohei Okubo, upon which this patent application is based, is hereby incorporated by reference.

BACKGROUND OF THE INVENTION

Field of the Invention

The present invention relates to an X-ray imaging apparatus.

Description of the Background Art

Conventionally, an X-ray imaging apparatus configured to display a model that visualizes a dose of X-rays irradiated on a surface of a patient is known. Such an X-ray imaging apparatus is disclosed, for example, in U.S. Patent Application Publication No. 2011-0317815.

U.S. Patent Application Publication No. 2011-0317815 discloses an X-ray imaging apparatus configured to display a model that visualizes a dose of X-rays irradiated on a surface of a patient. The X-ray imaging apparatus described in the above-described U.S. Patent Application Publication No. 2011-0317815 is configured to provide a three-dimensional model of a surface of a patient and calculate the dose of X-rays irradiated on the surface of the patient. The X-ray imaging apparatus is configured to display the three-dimensional model and visualize the calculated dose on the three-dimensional model. Further, the X-ray imaging apparatus described in the above-described U.S. Patent Application Publication No. 2011-0317815 is configured such that the displayed angular position of the visualized three-dimensional model moves in synchronization with the movement of the angular position at which the X-ray imaging apparatus is placed.

An X-ray imaging apparatus as described in, e.g., the above-described U.S. Patent Application Publication No. 2011-0317815 is used in interventional radiology (IVR: Interventional Radiology). When performing treatment while emitting X-rays in interventional radiology, the treatment needs to be performed while changing the irradiation position based on the skin dose so that the skin dose in the same irradiation position does not exceed a certain value.

However, as in the above-described U.S. Patent Application Publication No. 2011-0317815, when displaying the magnitude of the dose on a schematic three-dimensional model, it is considered to be difficult to match the dose displayed on the three-dimensional model with the dose that the patient has actually been exposed because actual patients are different in body shape and size and a position where a patient is placed on a top board is not the same. Therefore, as in the above-described U.S. Patent Application Publication No. 2011-0317815, in cases where a three-dimensional model of a patient is generated and a skin dose is displayed on the three-dimensional model, it is considered that it cannot be accurately displayed (the accuracy deteriorates). Therefore, it is difficult to make an operator recognize a position having a higher skin dose while suppressing the deterioration of the accuracy.

SUMMARY OF THE INVENTION

The present invention has been made to solve the above-described problems, and an object of the present invention is to provide an X-ray imaging apparatus capable of making an operator easily recognize a position high in skin dose while suppressing the deterioration of the accuracy.

In order to achieve the above-described object, an X-ray imaging apparatus according to one aspect of the present disclosure includes: a top board configured to place a subject thereon; an imaging unit provided with an X-ray irradiation unit including an X-ray source for emitting X-rays to a subject, and an X-ray detection unit for detecting the X-rays emitted from the X-ray irradiation unit; a moving unit configured to change an irradiation position which is a position of the subject to be irradiated with the X-rays by moving at least one of the imaging unit and the top board to irradiate the subject with the X-ray; and a control unit configured to perform control for displaying on a first display unit a two-dimensional virtual plane image which is a two-dimensional image in which an image indicating a skin dose for each of a plurality of irradiation positions and a scale image indicating at least one of a distance and an angle with respect to a reference position are superimposed on a virtual plane.

In the X-ray imaging apparatus according to the above-described one aspect of the present invention, the control unit is configured to perform control for displaying on a first display unit a two-dimensional virtual plane image which is a two-dimensional image in which an image indicating a skin dose for each of a plurality of irradiation positions and a scale image indicating at least one of a distance and an angle with respect to a reference position are superimposed on a virtual plane.

With this, the operator (surgeon) can visually recognize the magnitude of the skin dose at each of the plurality of irradiation positions on the two-dimensional virtual plane. Further, the operator can accurately recognize the skin dose distribution based on at least one of the distance and the angle with respect to the reference position, regardless of the body shape of the subject, based on the scale image and the skin dose on the two-dimensional virtual plane. As a result, unlike the case in which the method of displaying the magnitude of the skin dose on the three-dimensional model of the subject is used, it is possible to make the operator easily recognize the position high in skin dose while suppressing the deterioration of the accuracy.

BRIEF DESCRIPTION OF THE DRAWINGS

FIG. 13A is a diagram for explaining a first image for a head and a second image for a head according to a second embodiment and is a diagram showing the first image for a head.

FIG. 13B is a diagram for explaining a first image for a head and a second image for a head according to a second embodiment and is a diagram showing the second image for a head.

FIG. 14 is a block diagram showing an entire configuration of an X-ray imaging apparatus according to a third embodiment.

DESCRIPTION OF THE PREFERRED EMBODIMENT

Hereinafter, an embodiment in which the present invention is embodied will be described with reference to the attached drawings.

First Embodiment (Configuration of X-Ray Imaging Apparatus)

Referring to FIG. 1 to FIGS. 8A and 8B, the entire configuration of an X-ray imaging apparatus 100 according to a first embodiment of the present invention will be described.

Figure 1:
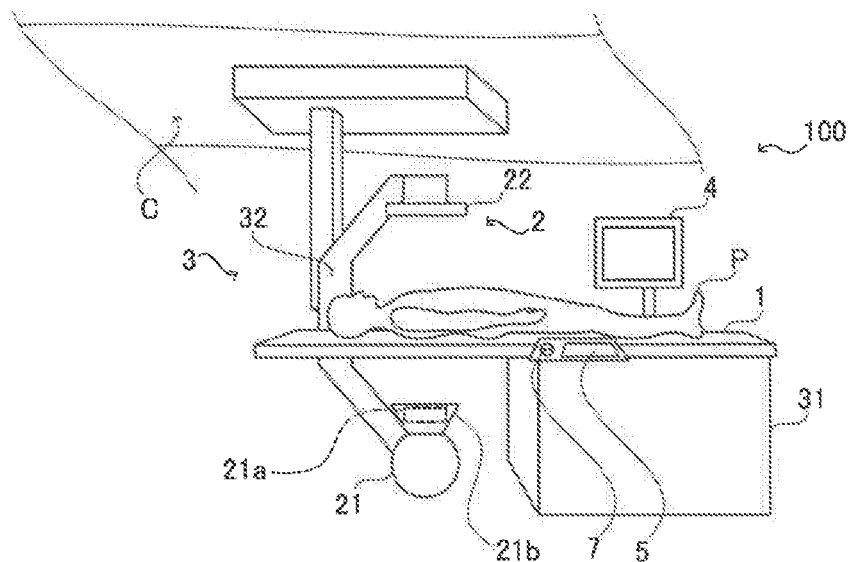
FIG. 1 is a front view for explaining a configuration of an X-ray imaging apparatus according to a first embodiment.
Figure 1:
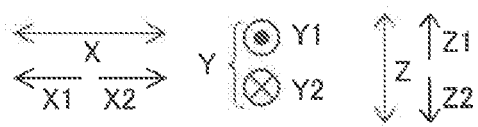

The X-ray imaging apparatus 100 according to the first embodiment of the present invention is, as shown in FIG. 1, a device for capturing an X-ray image A imaged an inside of a subject P by irradiating the subject P such as a human body with X-rays from the outer side of the subject P. An operator using the X-ray imaging apparatus 100 can perform various types of treatments by inserting a treatment instrument such as a catheter into a blood vessel (e.g., a blood vessel of a heart of the subject P) of the subject P while visually recognizing the X-ray image A of the subject P.

Note that in this specification, the term "operator" is not limited to a person who performs treatment of a subject P and is described to also include a "manipulator" that simply manipulates the X-ray imaging apparatus 100 without directly participating in the treatment of the subject P.

Figure 2:
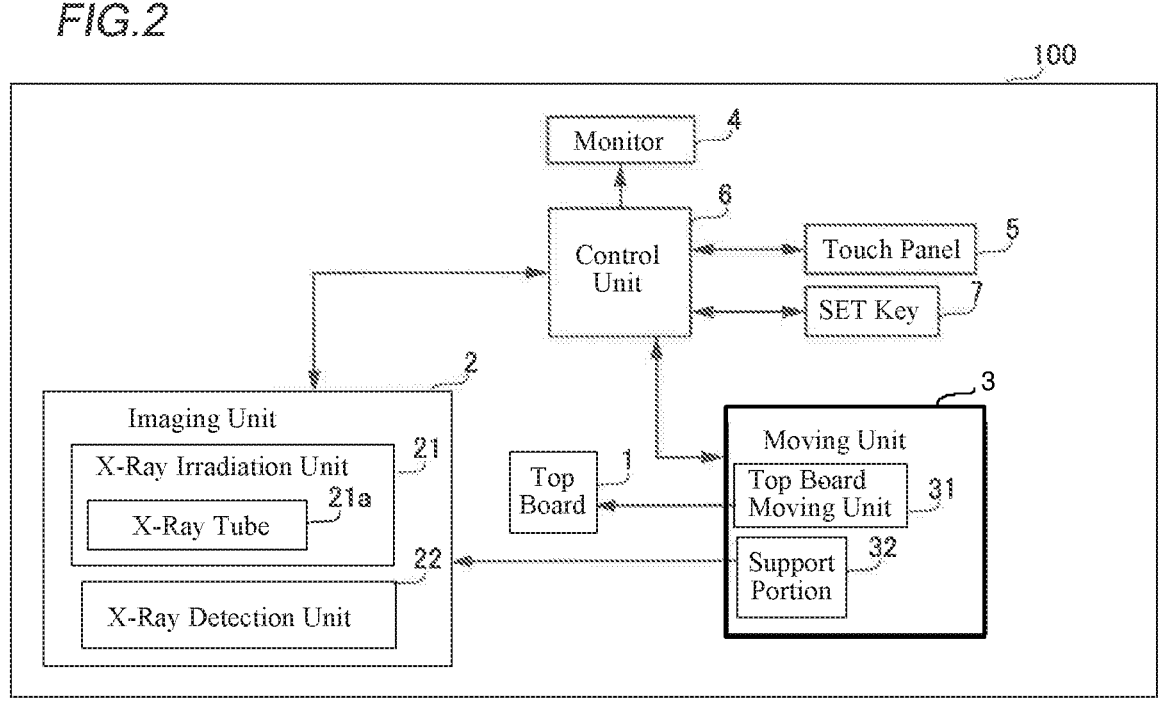
FIG. 2 is a block diagram showing an entire configuration of an X-ray imaging apparatus according to a first embodiment.

As shown in FIG. 1 and FIG. 2, the X-ray imaging apparatus 100 is provided with a top board 1, an imaging unit 2, a moving unit 3 including a top board moving unit 31 and a support portion 32, a monitor 4, a touch panel 5, a control unit 6, and a SET key 7. Note that the monitor 4 is an example of the "first display unit" recited in claims. Further note that the touch panel 5 is an example of the "operation unit" recited in claims. Further note that the touch panel 5 serves as the "second display unit" recited in claims. That is, the touch panel 5 is an example in which the "operation unit" and the "second display unit" recited in claims are integrated.

(Composition of Each Part of X-Ray Imaging Apparatus)

As shown in FIG. 1 and FIG. 2, the top board 1 is configured as an examination table on which a subject P is placed when performing X-ray imaging. The top board 1 is movably supported in the horizontal direction (the direction parallel to the X-Y plane in FIG. 1) and the vertical direction (the direction parallel to the Z-direction in FIG. 1) by a top board moving unit 31 which will be described later, As shown in FIG. 1 and FIG. 2, the imaging unit 2 captures an X-ray image A of a subject P. The imaging unit 2 includes an X-ray irradiation unit 21 for irradiating the subject P with X-rays and an X-ray detection unit 22 for detecting the X-rays emitted from the X-ray irradiation unit 21. The X-ray irradiation unit 21 and the X-ray detection unit 22 are arranged so as to face each other with the top board 1 on which the subject P is placed interposed therebetween. The X-ray irradiation unit 21 and the X-ray detection unit 22 are movably supported by a support portion 32 which will be described later.

The X-ray irradiation unit 21 includes an X-ray source 21a and a collimator 21b. The X-ray source 21a is connected to a high voltage generating unit (not shown) to generate X-rays when a high voltage is applied and is an X-ray tube for irradiating the subject P with the generated X-rays. The X-ray source 21a is arranged with the X-ray emission direction facing the detecting surface of the X-ray detection unit 22. The collimator 21b is configured to adjust the irradiation field of the X-rays emitted by the X-ray source 21a. The X-ray irradiation unit 21 is connected to a control unit 6 which will be described later. The control unit 6 controls the X-ray irradiation unit 21 in accordance with preset imaging conditions, such as, e.g., a tube voltage, a tube current, and a time-interval of X-ray irradiation, to generate X-rays from the X-ray source 21a.

The X-ray detection unit 22 detects the X-rays emitted from the X-ray irradiation unit 21 and transmitted through the subject P and outputs a detection signal corresponding to the detected X-ray intensity. The X-ray detection unit 22 is composed of, for example, an FPD (Flat Panel Detector). The X-ray detection unit 22 is connected to the control unit 6 which will be described later. The control unit 6 generates an X-ray image A based on signals output by the X-ray detection unit 22.

The moving unit 3 moves at least one of the top board 1 and the imaging unit 2 to change the irradiation position R which is a position of the subject P irradiated with X-rays. Specifically, the moving unit 3 includes the top board moving unit 31 and the support portion 32. The top board moving unit 31 is configured to move the top board 1 in the horizontal direction (direction parallel to the X-Y plane in FIG. 1) and the vertical direction (direction parallel to the Z-direction in FIG. 1). The support portion 32 is attached to the ceiling C and supports the X-ray irradiation unit 21 and the X-ray detection unit 22 so as to face each other with the top board 1 on which a subject P is placed interposed therebetween. The support portion 32 supports the position and the angle of the imaging unit 2 in a changeable manner. The support portion 32 supports the X-ray irradiation unit 21 and the X-ray detection unit 22 with the distance therebetween changeable.

Figure 3:
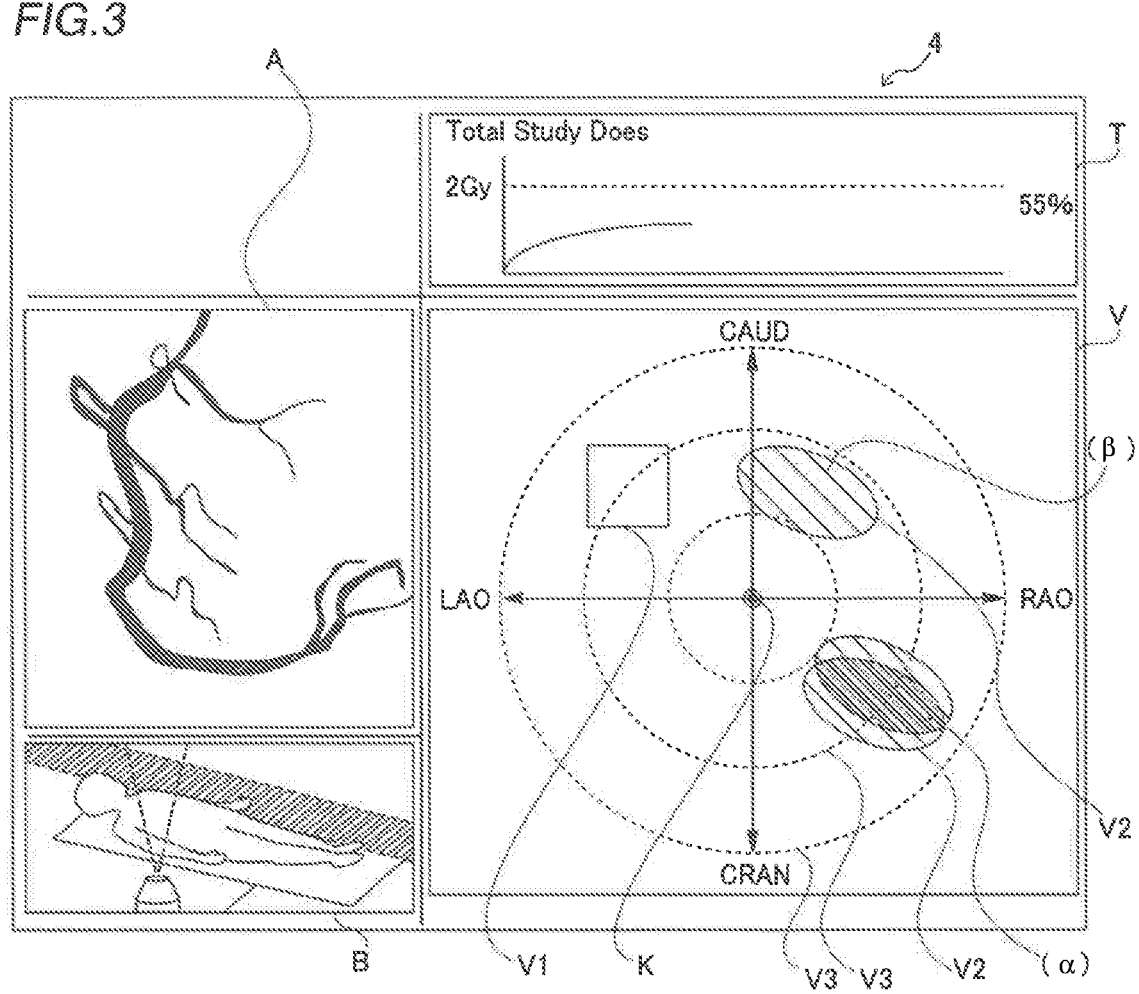
FIG. 3 is a diagram for explaining an image displayed on a monitor according to a first embodiment.

As shown in FIG. 3, the monitor 4 is configured to display a two-dimensional virtual plane image V, a skin dose total amount image T, an X-ray image A, and a position image B side by side according to an instruction from the control unit 6 which will be described later. The monitor 4 includes, for example, a display monitor which is a device for displaying video signals of a still image or a moving image output from a device such as a computer. Note that the detailed description of the images displayed on the monitor 4 will be described later.

The touch panel 5 accepts inputs for operating the X-ray imaging apparatus 100. That is, the touch panel 5 accepts an operation of determining an irradiation position R to perform X-ray imaging from among a plurality of irradiation positions R. Further, the touch panel 5 is configured to display a display of the irradiation position R. The images to be displayed on the touch panel 5 will be described in detail later.

The control unit 6 is a computer including a CPU (Central Processing Unit), a ROM (Read Only Memory), a RAM (Random Access Memory), and the like. The control unit 6 controls the operation of the X-ray imaging apparatus 100 based on the operation by an operator. That is, the control unit 6 performs X-ray imaging by controlling the imaging unit 2 to generate an X-ray image A. Besides, the control unit 6 performs control for arranging the two-dimensional virtual plane image V, the skin dose total amount image T, the X-ray image A, and the position image B and displaying them on the monitor 4. Further, the control unit 6 performs control for displaying position information images D on the touch panel 5. Further, the control unit 6 is configured to determine at which irradiation position R among a plurality of irradiation positions R the X-ray imaging is to be performed based on the input operation on the touch panel 5. And, the control unit 6 changes the position of the imaging unit 2 by controlling the operation of the moving unit 3.

A SET key 7 is provided separately from the touch panel 5 and accepts an operation for moving the imaging unit 2 to a position for emitting X-rays toward a determined irradiation position Rd. In other words, the control unit 6 controls the moving unit 3 to move the imaging unit 2 to a position for emitting X-rays toward the determined irradiation position Rd while the SET key 7 is being pressed by an operator.

(Displays on Monitor)

Here, in the first embodiment, as shown in FIG. 3, the two-dimensional virtual plane image V is a two-dimensional image in which an irradiation position image V1 which is an image indicating the current irradiation position R1 is indicated, a skin dose image V2 which is an image indicating a skin dose, a reference point K indicating a reference position, and a scale image V3 indicating at least one of the distance and the angle with respect to the reference position K are superimposed on a virtual plane.

The irradiation position image V1 is an image indicating the position and the range of the current irradiation position R1 among the plurality of irradiation positions R at which X-ray irradiation is performed. As shown in FIG. 3, the irradiation position image V1 is indicated by a quadrilateral. By moving the moving unit 3, the position and the angle of the top board 1 and the imaging unit 2 are changed. Thereby, since at least one of the position and the range of the current irradiation position R1 is changed, at least one of the position and the size of the irradiation position image V1 in the two-dimensional virtual plane image V is changed according to the position and the range of the current irradiation position R1. Further, since the range in the subject P in which X-rays are emitted is changed in accordance with the distance between the X-ray irradiation unit 21 and the X-ray detection unit 22 and the operation of the collimator 21b, the size of the irradiation position image V1 is changed in accordance with the range in which X-rays are emitted.

Figure 4:
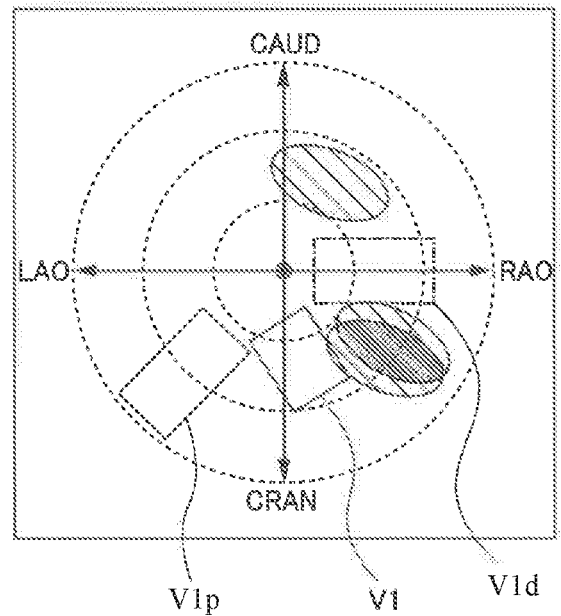
FIG. 4 is a diagram for explaining that an image showing an irradiation position on a monitor is changed based on a determination and a change of the irradiation position according to a first embodiment.

When it is determined at which irradiation position R the X-ray imaging is to be performed, the control unit 6 performs control for displaying on the monitor 4 a two-dimensional virtual plane image V in which an image V1d indicating the determined irradiation position Rd is displayed at a position corresponding to the determined irradiation position Rd on the virtual plane so that the position corresponding to the determined irradiation position Rd can be visually distinguished. For example, as shown in FIG. 4, before moving the imaging unit 2, when it is determined at which irradiation position R the X-ray imaging is to be performed, an image V1d indicating the determined irradiation position Rd is displayed on the two-dimensional virtual plane image V.

Further, during the period in which the imaging unit 2 is being moved in order to emit X-rays to the determined irradiation position Rd, it is controlled so that the image V1p showing the original irradiation position Rp is indicated by a dotted line, the image V1d showing the determined irradiation position Rd is indicated by a dashed-dotted line, and the irradiation position image V1 showing the current irradiation position R1 during the movement is indicated by a solid line. During the period in which the determination is valid (i.e., the period in which the SET key 7 is being pressed to move the imaging unit 2 to the position for emitting X-rays to the determined irradiation position Rd or the period in which the movement is canceled), the image V1p showing the original irradiation position Rp and the image V1d showing the irradiation position Rd in which the movement destination is determined are displayed.

The skin dose image V2 is an image showing the skin dose of each of the plurality of irradiation positions R so as to visually indicate the magnitude of the skin dose. Specifically, as shown in FIG. 3, the skin dose image is an image obtained by approximating the skin dose of each of the plurality of irradiation positions R in an elliptical shape. In addition, it is configured such that the ellipse is colored based on the magnitude of the skin dose so that the skin dose accumulated in each irradiation position R can be visually recognized. For example, it is configured so that the magnitude of the skin dose can be identified by color. For example, the irradiation position R which can be further irradiated with X-rays in the future due to the small skin dose is indicated by green, and the irradiation position Rn which is not recommended to be further irradiated with X-rays due to the large skin dose is indicated by red. Specifically, in FIG. 3, the portion indicated by the portion (α) is a position where further X-ray irradiation is not recommended due to the large skin dose, and the portion indicated by the portion (β) is a position where further X-ray irradiation can be performed due to the small skin dose.

The scale image V3 is provided with a scale in a circular shape centered on the reference point K so as to indicate at least one of the distance and the angle with respect to the reference position and is formed two-dimensionally so as to include substantially the entire movable range of the moving unit 3. As shown in FIG. 3, in the scale image V3, the concentric scale centered on the reference point K is provided, taking the irradiation position R when the moving unit 3 is at a reference position as the reference point K. With the reference point K which is the center of the circle set to 0, it is configured to indicate the angle or the distance that increases in value as it advances toward the outer scale. For example, in the imaging as shown in FIG. 3, an example of performing treatment of a heart is shown in which X-ray imaging is performed while changing the angle of the support portion 32 without changing the position of the support portion 32 and the height thereof from the floor surface and the distance between the X-ray irradiation unit 21 and the X-ray detection unit 22.

As shown in FIG. 3, the skin dose total amount image T is an image showing the total amount of the skin dose of the subject P during the operation. That is, the skin dose total amount image T is an image shown on the monitor 4 by a display using specific numerical values and a graph so that the total amount of each skin dose in a plurality of irradiation positions R calculated from the time point when the X-ray imaging is initiated can be visually recognized. In other words, the image indicates the total amount of the skin dose on the entire body surface of the subject P. The skin dose total amount image T is displayed, for example, along with the two-dimensional virtual plane image V side by side in the up-down direction on the monitor 4.

As shown in FIG. 3, the X-ray image A is an image indicating the inside of the subject P based on the detection signal of the X-rays transmitted through the subject P. The X-ray image A is continuously acquired so that the operator can observe the inside of the subject P in real-time. And, the X-ray image A is configured to be displayed on the monitor 4 as a moving image. The X-ray image A is displayed, for example, along with the two-dimensional virtual plane image V side by side in the left-right direction on the monitor 4.

The position image B is a visual indication of the current position and angle of the imaging unit 2 and the top board 1, as shown in FIG. 3. The position image B is displayed, for example, together with the two-dimensional virtual plane image V side by side in the left-right direction on the monitor 4.

(Displays on Touch Panel)

Figure 5:
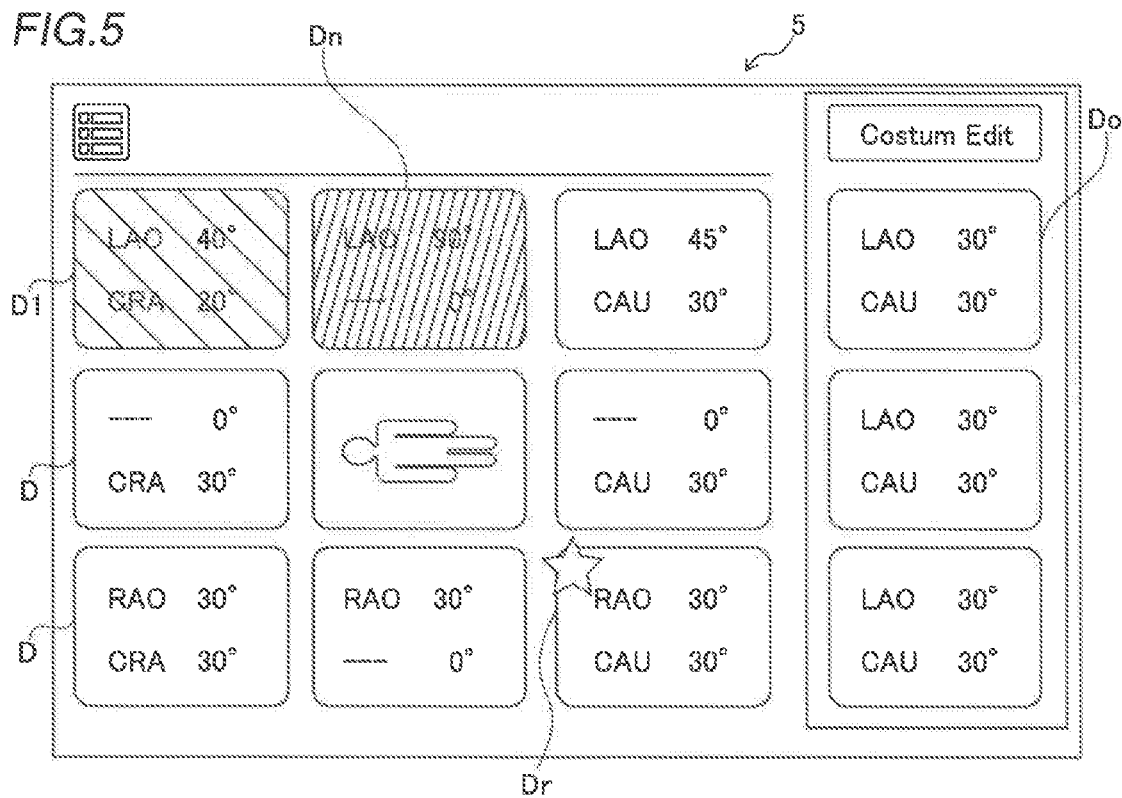
FIG. 5 is a diagram for explaining images displayed on a touch panel according to a first embodiment.

As shown in FIG. 5, the touch panel 5 is configured to display position information images D each corresponding to the plurality of irradiation positions R based on the irradiation position R and the skin dose. For example, the position information image D is an image showing the information about the positions of the top board 1 and the imaging unit 2 in a visually discriminable manner for each of the plurality of irradiation positions R. The control unit 6 is configured to display the plurality of position information images D on the touch panel 5 as a list.

Further, the control unit 6 is configured to display the current position information image D1, which is an image indicating the information about the current irradiation position R1, among the plurality of position information images D displayed as a list in a visually discriminable manner on the touch panel 5. Specifically, the background of the plurality of position information images D displayed as a list is white, but unlike this, it is configured to be visually distinguishable by displaying the background of the current position information image D1 in blue.

Further, the control unit 6 is configured to display on the touch panel 5 the non-recommended position information image Dn among the plurality of position information images D displayed as a list which is an image indicating information about the non-recommended irradiation position Rn in a visually distinguishable manner. That is, the control unit 6 is configured to make the touch panel 5 display the irradiation position R in which the skin dose exceeds a predetermined threshold among the plurality of irradiation positions R as a non-recommended irradiation position Rn in a visually distinguishable manner. Specifically, the background of the plurality of position information images D displayed as a list are white, but unlike this, it is configured to be visually distinguishable by displaying the background of the non-recommended position information image Dn in red.

Further, the control unit 6 is configured to display on the touch panel 5 the recommended position information image Dr which is an image indicating the information about the recommended irradiation position Rr among the plurality of position information images D displayed as a list in a visually distinguishable manner. That is, the control unit 6 is configured to display on the touch panel 5 a display indicating that the irradiation position R is the irradiation position Rr recommended to perform X-ray imaging from among the plurality of irradiation positions R based on the irradiation position R and the skin dose in a visually distinguishable manner. Specifically, a star mark is added to the position information image D corresponding to the recommended irradiation position Rr among the plurality of position information images D, and the image with the star mark is displayed on the touch panel 5 as the recommended position information image Dr. The recommended irradiation position Rr is selected based on the region of the subject P to be treated or examined, from the information input by the operator in advance, the database stored in the system, the database acquired through the network, and the like.

Further, the control unit 6 is configured so that a desired irradiation position Ro can be registered in advance by an operator. The desired position information image Do based on the registered desired irradiation position Ro is configured to be displayed on the touch panel 5. Note that it may be configured such that the desired irradiation position Ro can be selected from the database stored in the system or the database acquired through the network depending on the region of the subject P to be imaged.

(Control Depending Region To Be Imaged)

As shown in FIGS. 6A and 6B to FIGS. 8A and 8B, the control unit 6 is configured to generate a two-dimensional virtual plane image V so that the virtual plane and the top board 1 in the two-dimensional virtual plane image V displayed on the monitor 4 are oriented in parallel to each other and display the two-dimensional virtual plane image V on the monitor 4. That is, the control unit 6 is configured to generate an image V10 for a heart or an image V20 for a leg so that the virtual plane and the top board 1 are oriented in parallel to each other and displayed on the monitor 4 when performing X-ray imaging on the heart of the subject P and the leg thereof. Note that the image V10 for a heart and the image V20 for a leg are examples of the "image for a heat and a leg" recited in claims.

As an example of imaging a heart of a subject P, the image V10 for a heart is a two-dimensional virtual plane image V used, for example, to perform X-ray imaging while changing the angle of the support portion 32 while not changing the position of support portion 32 and the height thereof from the floor, the distance between the X-ray irradiation unit 21 and the X-ray detection unit 22.

Figure 6A:
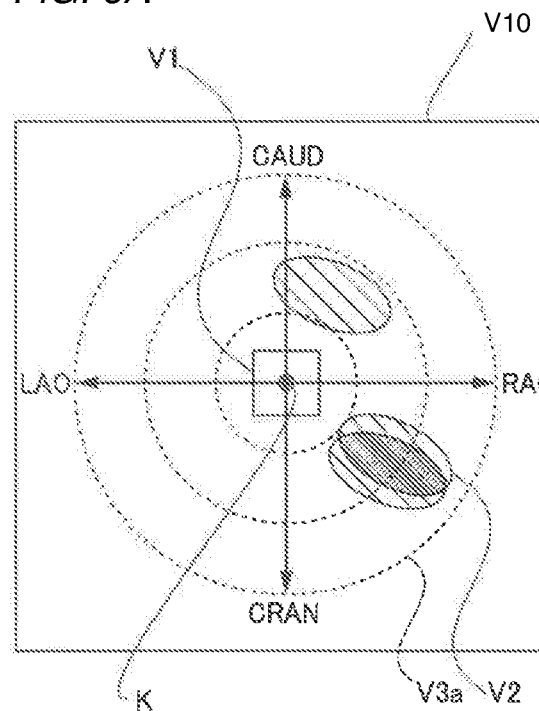
FIG. 6A is a diagram for explaining an image for a heart according to a first embodiment and is a diagram in which an irradiation position is in a reference position.
Figure 6B:
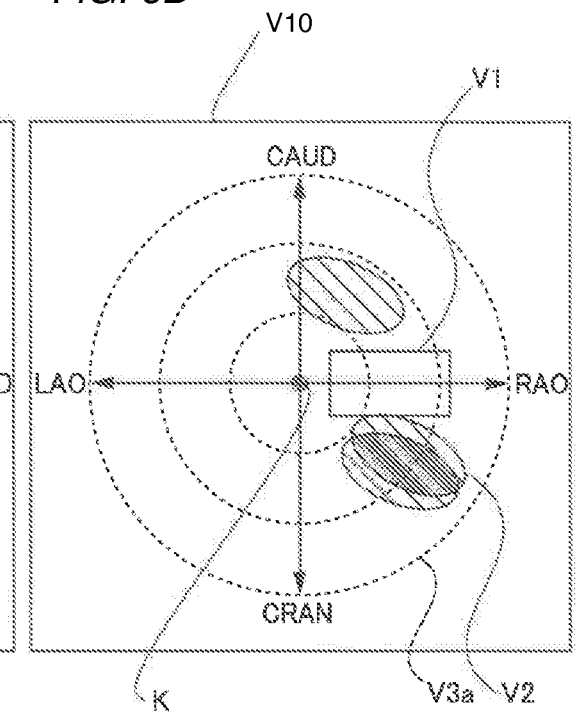
FIG. 6B is a diagram for explaining an image for a heart according to a first embodiment and a diagram in which an irradiation position is moved in an RAO-direction.

In the image V10 for a heart, the scale image V3 is a scale image V3a indicating the angle with respect to the reference position and is configured to indicate the angular position of the support portion 32. Specifically, the angle of the subject Pin the up-down direction and the angle of the subject P in the left-right direction are displayed in a distinguishable manner. That is, the head direction (CAUD: Caudal) and the leg direction (CRAN: Cranial), the right-hand direction (RAO: Right Anterior Oblique view), and the left-hand direction (LAO: Left Anterior Oblique view) are displayed in a distinguishable manner. With the reference point K which is the center of the circle set to 0, it is configured to show an angle having a value that becomes larger as it advances toward the outer scale. For example, although FIG. 6A shows an image V10 for a heart which is a two-dimensional virtual plane image V when the imaging unit 2 is positioned at the reference position (a position in which the angle is inclined neither in the up-down direction nor in the left-right direction and the X-ray irradiation unit 21 and the X-ray detection unit 22 are arranged in parallel in the vertical direction), FIG. 6B shows an image V10 for a heart which is a two-dimensional virtual plane image V when the angle of the support portion 32 is changed in the direction of the RAO (right Anterior Oblique view).

Figure 7A:
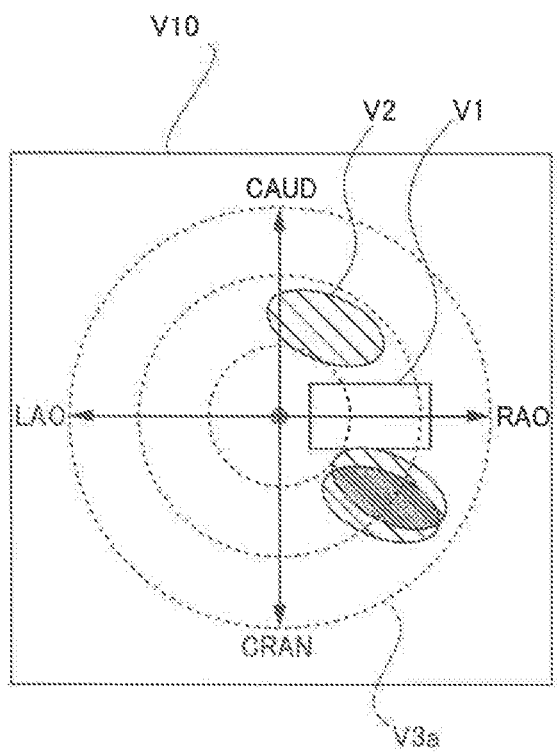
FIG. 7A is a diagram for explaining an operation when a top board is translated in an image for a heart according to a first embodiment and shows a diagram before moving a top board.
Figure 7B:
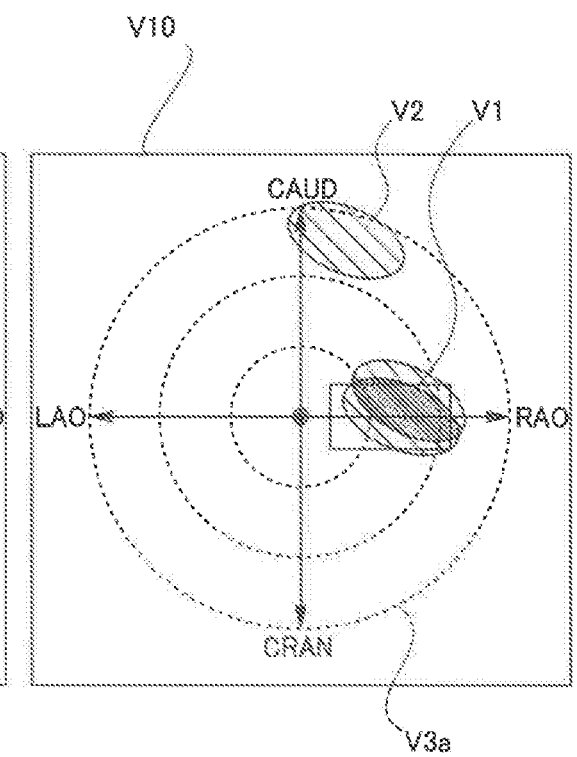
FIG. 7B is a diagram for explaining an operation when a top board is translated in an image for a heart according to a first embodiment and shows a diagram after the top board is moved.

Note that, as shown in FIG. 7A and FIG. 7B, in cases where the position of the top board 1 is moved by the top board moving unit 31 in the horizontal direction (direction parallel to the X-Y plane in FIG. 1) when performing a display using the image V10 for a heart which is a two-dimensional virtual plane image V including the scale image V3a indicating the angle of the support portion 32, the distribution of the skin dose is updated as shown in FIG. 7A and FIG. 7B. For example, as shown in FIG. 7A and FIG. 7B, when the top board 1 is moved in the direction toward the head of the subject P, the distribution of the skin dose images V2 is updated from FIG. 7A to FIG. 7B.

Further, as an example when performing imaging of a leg of a subject P, for example, the image V20 for a leg is a two-dimensional virtual plane image V used when performing X-ray imaging while translating the top board 1 in the horizontal direction (direction parallel to the X-Y plane in FIG. 1) without changing the position of the support portion 32 and the angle thereof.

Figure 8A:
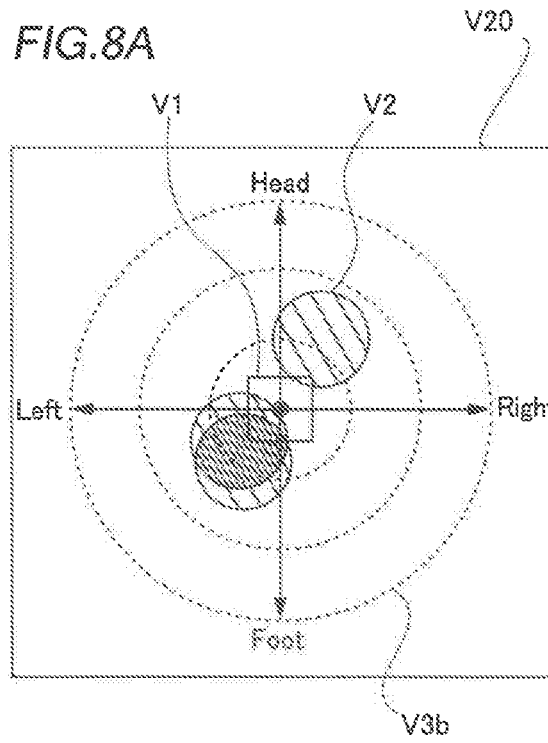
FIG. 8A is a diagram for explaining an image for a leg according to a first embodiment and shows a diagram in which an irradiation position is in a reference position.
Figure 8B:
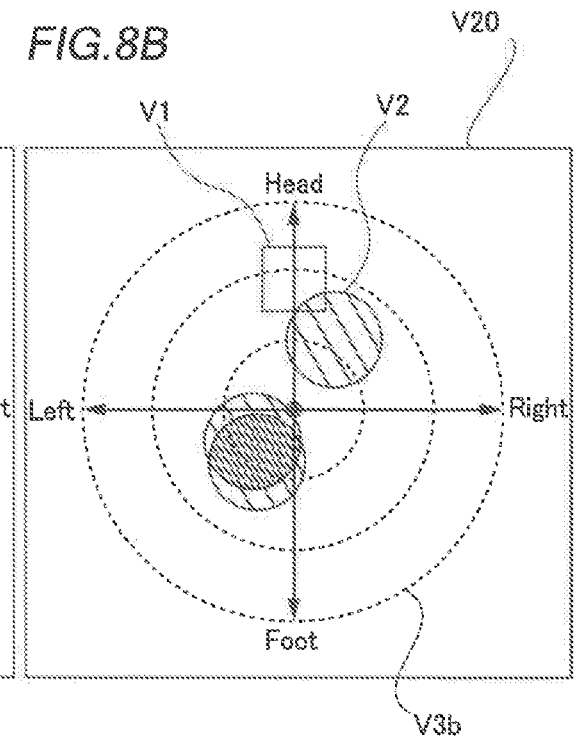
FIG. 8B is a diagram for explaining an image for a leg according to a first embodiment and shows an image in which an irradiation position is moved in the Head-direction.

As shown in FIG. 8A and FIG. 8B, in the image V20 for a leg, the scale image V3 is a scale image V3b indicating the distance with respect to the reference position and is configured to indicate the position in the horizontal plane of the top board 1. Specifically, the position of the subject P in the up-down direction and the position of the subject P in the left-right direction are displayed in a distinguishable manner. That is, the head direction (Head) and leg direction (Foot) and the right-hand direction (Right) and left-hand direction (Left) are displayed so as to be distinguishable. With the reference point K which is the center of the circle set to 0, it is configured to show that the distance becomes a larger value as it advances toward the outer scale. For example, while FIG. 8A shows an image V20 for a leg which is a two-dimensional virtual plane image V when the imaging unit 2 is positioned at the reference position, FIG. 8B shows an image V20 for a leg which is a two-dimensional virtual plane image V when the irradiation position R is moved toward the Head by changing the position of the top board 1.

(Control Processing in First Embodiment)

Figure 9:
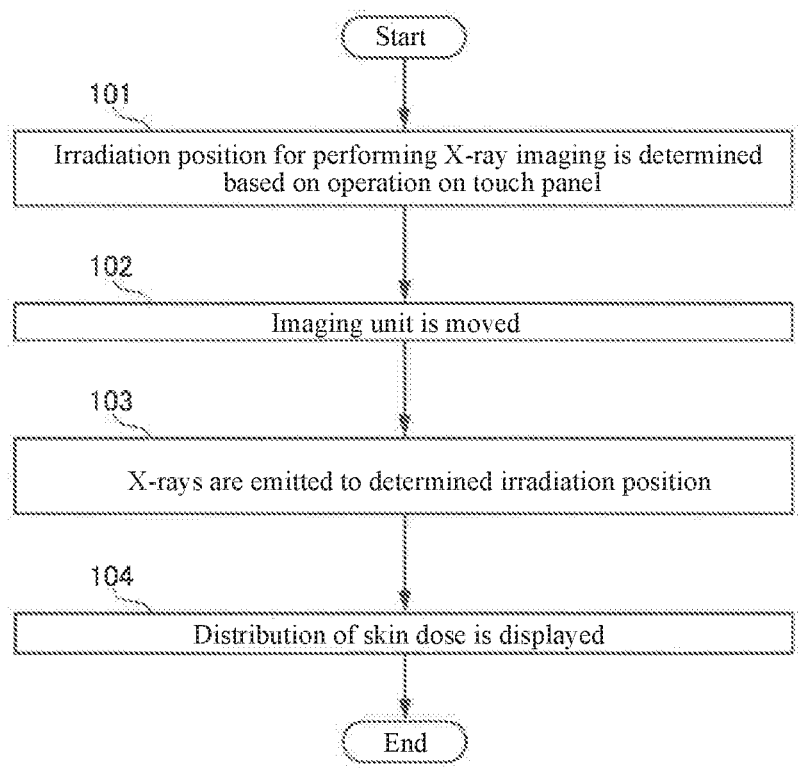
FIG. 9 is a flowchart for explaining control processing of an X-ray imaging apparatus according to a first embodiment.

Next, referring to FIG. 9, a control processing flow relating to X-ray imaging by the X-ray imaging apparatus 100 by the first embodiment will be described. Step 101 to Step 104 shows the control processing by the control unit 6.

First, in Step 101, an irradiation position R which is the position of the subject P where X-ray imaging is to be performed is determined based on the operation on the touch panel 5. Then, the image V1d indicating the determined irradiation position Rd is displayed on the two-dimensional virtual plane image V.

Next, in Step 102, the imaging unit 2 is moved to a position for emitting X-rays to the determined irradiation position Rd while the SET key 7 is being pressed. Then, while the determination is valid, the image V1p indicating the original irradiation position Rp, the image V1d indicating the determined irradiation position Rd, and the irradiation position image V1 indicating the moving current irradiation position R1 are displayed on the two-dimensional virtual plane image V.

Next, in Step 103, the X-rays are emitted to the determined irradiation position Rd to perform X-ray imaging.

Next, in Step 104, a skin dose image V2 is displayed on the two-dimensional virtual plane image V.

Effects of First Embodiment

In this first embodiment, the following effects can be obtained.

The X-ray imaging apparatus 100 according to the first embodiment is provided with the top board 1 configured to place a subject P thereon; the imaging unit 2 composed of the X-ray irradiation unit 21 including the X-ray source 21a for irradiating the subject P with the X-rays and the X-ray detection unit 22 for detecting the X-rays emitted from the X-ray irradiation unit 21; a moving unit 3 configured to change the irradiation position R which is a position of the subject P to be irradiated with X-rays by moving at least one of the imaging unit 2 and the top board 1 to irradiate the subject P with the X-rays; and a control unit 6 configured to perform control for displaying on the monitor 4 (first display unit) the two-dimensional virtual plane image V which is a two-dimensional image in which the skin dose image V2 which is an image indicating the skin dose for each of the plurality of irradiation positions R and the scale image V3 indicating at least one of the distance and the angle with respect to the reference position are superimposed on the virtual plane control.

Further, in the X-ray imaging apparatus 100 of the first embodiment, with the above-described configuration, the control unit 6 is configured to perform control for displaying on the monitor 4 the two two-dimensional virtual plane image V which is a two-dimensional image in which the skin dose image V2 which is an image indicating the skin dose for each of the plurality of irradiation positions R and the scale image V3 indicating at least one of the distance and the angle with respect to the reference position are superimposed on the virtual plane.

With this, the operator (surgeon) can visually recognize the magnitude of the skin dose at each of the plurality of irradiation positions R on the two-dimensional virtual plane. Further, the operator can accurately recognize the skin dose distribution based on at least one of the distance and the angle with respect to the reference position, regardless of the body shape of subject P, based on the scale image V3 and the skin dose on the two-dimensional virtual plane. As a result, unlike the case of using the method of displaying the magnitude of the skin dose on the three-dimensional model of the subject P, it is possible to make the operator easily recognize the position high in skin dose while suppressing the deterioration of the accuracy.

Further, in the first embodiment, further effects can be obtained by the following configuration.

That is, in the first embodiment, the control unit 6 is configured to perform control for displaying on the monitor 4 (first display unit) the two-dimensional virtual plane image V in which the skin dose image V2 which is an image indicating the skin dose for each of the plurality of irradiation positions R, the scale image V3 which is formed two-dimensionally so as to include substantially the entire movable range of the moving unit 3 and indicates at least one of the distance and the angle with respect to the reference position, and the irradiation position image V1 which is an image indicating the current irradiation position R1, are superimposed on the virtual plane.

With this configuration, substantially all of the plurality of irradiation positions R can be indicated by a single two-dimensional virtual plane image V. As a result, since the magnitudes of the skin doses in substantially all of the irradiation positions R can be simultaneously identified in the same image, the irradiation position R can be more easily determined so that the skin dose at the moving destination does not exceed the predetermined value when moving the imaging unit 2 to perform X-ray imaging.

Further, in the first embodiment, the control unit 6 is configured to display on the monitor 4 (first display unit) the two-dimensional plane image V including the skin dose image V2 which is an image indicating the skin dose so as to visually indicate the magnitude of the skin dose, the reference point K indicating the reference position, the scale image V3 provided with a circular scale centered on the reference point K, the two-dimensional virtual plane image V indicating a reference position so as to show at least one of the distance and the angle with respect to the reference position, and the irradiation position image V1 indicating the current irradiation position R1. With this configuration, the relative positional relationship between the skin dose and the current irradiation position R1 on the virtual plane can be visually identified. Therefore, it is possible to easily determine the irradiation position R for performing X-ray imaging while avoiding the position where the skin dose is already large.

In addition, in the first embodiment, the control unit 6 is configured to display the skin dose total amount image T which is an image indicating the total amount of the skin dose of the subject P during the operation and the two-dimensional virtual plane image V side by side on the monitor 4 (first display unit).

Note that when performing the interventional radiology, the skin dose of each of the plurality of irradiation positions R should not exceed a certain value, and the total amount of the skin dose of the subject P during the operation also should not exceed a certain value. In this regard, with the configuration of the first embodiment, the operator can simultaneously visually distinguish the skin dose for each of the plurality of irradiation positions R and the total amount of the skin dose of the subject P during the operation. Therefore, it is possible to consider not only the timing of changing the irradiation position R but also the timing at which it is required to judge whether to continue the treatment itself in order to prevent the dose from exceeding a certain level in the whole-body exposure of the subject P.

Furthermore, the first embodiment is further provided with an operation unit (touch panel 5) for accepting an operation for determining the irradiation position R to perform X-ray imaging from among the plurality of irradiation positions R. The operation unit (touch panel 5) includes a second display unit (touch panel 5) for displaying a display related to the irradiation position R. The control unit 6 is configured to display on the touch panel 5 a display indicating the irradiation position Rr in which the irradiation position R is recommended to perform X-ray imaging, from among the plurality of irradiation positions R in a visually distinguishable manner, based on the irradiation position R and the skin dose.

By configuring as described above, the operator can easily determine which irradiation position R among the plurality of irradiation positions R is suitable for X-ray imaging by visually recognizing the touch panel 5. Therefore, it is possible to reduce the workload that the operator confirms the magnitude of the skin dose when selecting the irradiation position R.

Also, in the first embodiment, the control unit 6 is configured to make the touch panel 5 (second display unit) display an image indicating the irradiation position R that the skin dose exceeds a predetermined threshold value among the plurality of the irradiation positions R as a non-recommended irradiation position Rn. By configuring as described above, the operator can easily recognize the non-recommended irradiation position Rn which is an irradiation position R in which it is better to avoid X-ray imaging due to the large skin dose, by visually recognizing the touch panel 5. Therefore, it is possible to easily continue the treatment while avoiding the irradiation position R having a large skin dose.

Further, in the first embodiment, the control unit 6 is configured to make the touch panel 5 display the position information images D each corresponding to the plurality of irradiation positions R on the touch panel 5 (second display unit) based on the irradiation positions R and the skin doses and is configured to determine at which irradiation position R the X-ray imaging is to be performed among the plurality of irradiation positions R based on the input operation on the touch panel 5 (operation unit).

By configuring as described above, it is possible to easily determine the irradiation position R suitable for X-ray imaging based on the plurality of position information images D. Therefore, it is possible to easily emit X-rays while avoiding a higher skin dose position.

Further, in the first embodiment, the control unit 6 is configured to make the monitor 4 (first display unit) display the two-dimensional virtual plane image V in which the image V1d indicating the determined irradiation position Rd is displayed at the position corresponding to the determined irradiation position Rd on the virtual plane when it is determined at which irradiation position R the X-ray imaging is to be performed so that the position corresponding to the determined irradiation position Rd can be visually recognized. By configuring as described above, the magnitude of the skin dose in the determined irradiation position Rd can be easily recognized by visually recognizing the displays on the two-dimensional virtual plane after the determination of the irradiation position R and before the movement of the imaging unit 2 to perform X-ray imaging at the determined irradiation position Rd. When the skin dose at the determined irradiation position Rd is large, the irradiation position Rd determined before the initiation of the X-ray imaging can be changed to perform X-ray imaging at a different irradiation position R. Therefore, it is easy to avoid the irradiation position R having a high skin dose even before initiating the movement of the imaging unit 2.

In addition, in the first embodiment, the control unit 6 is configured to make the touch panel 5 (second display unit) display a plurality of position information images D as a list and also make the touch panel 5 display the current position information image D1 which is an image indicating the information on the current irradiation position R1, the recommended position information image Dr which is an image indicating the information on the recommended irradiation position Rr, and the non-recommended position information image Dn which is an image indicating the information on the non-recommended irradiation position Rn, among the plurality of position information images D displayed as a list in a visually distinguishable manner.

By configuring as described above, it is possible to easily recognize which irradiation position R is suitable as the irradiation position R for performing X-ray imaging by checking the position information image D when determining the irradiation position R. As a result, the irradiation position R having a high skin dose can be easily avoided.

In addition, in the first embodiment, the control unit 6 is configured to generate the two-dimensional virtual plane image V so that the virtual plane and the top board 1 in the two-dimensional virtual plane image V displayed on the monitor 4 (first display unit) are oriented in parallel to each other, and make the monitor 4 display the two-dimensional virtual plane image V.

By configuring as described above, it is possible to generate the two-dimensional virtual plane so that the body surface of the subject P and the two-dimensional virtual plane are oriented in parallel to each other. As a result, the display of the skin dose on the two-dimensional virtual plane becomes a display from substantially the same direction as the skin dose on the body surface of the subject P. Therefore, the skin dose of the subject P can be more easily recognized by checking the skin dose on the two-dimensional virtual plane.

Further, in the first embodiment, the control unit 6 is configured to generate the image for a heat and a leg (the image V10 for a heart and the image V20 for a leg) so that the virtual plane and the top board 1 are oriented in a direction parallel to each other when performing the X-ray imaging of the heart and the leg of the subject P and makes the monitor 4 display them.

By configuring as described above, when performing the X-ray imaging of the heart and the leg, the image V10 for a heart can indicate the skin dose when imaging the heart, and the image V20 for a leg can indicate the skin dose when imaging the leg. As a result, the configuration of the two-dimensional virtual plane image V can be changed in accordance with the operation of the imaging unit 2 based on the imaging region. Therefore, the skin dose of the body surface of the subject P can be displayed more accurately. Therefore, it is possible to easily recognize the position having a high skin dose in accordance with the position of the subject P and emit X-rays while avoiding the position having a high skin dose.

Further, in the first embodiment, the control unit 6 is configured to display the image captured by the imaging unit 2 and the two-dimensional virtual plane image V side by side on the monitor 4 (first display unit).

By configuring as described above, it is possible to easily recognize the skin dose in the current irradiation position R1 even in the case of performing the treatment while viewing the captured image. As a result, even when the operator performs treatment while viewing X-ray image A captured by the imaging unit 2, it is possible to more easily avoid the skin dose from exceeding a certain value in the current irradiation position R1.

Second Embodiment

Referring to FIG. 10 to FIGS. 13A and 13B, the configuration of an X-ray imaging apparatus 200 according to a second embodiment will be described. Unlike the X-ray imaging configured to perform X-ray imaging using a single imaging unit 2 (one set of the X-ray irradiation unit 21 and the X-ray detection unit 22), the second embodiment is configured to perform X-ray imaging by using two imaging units different from each other, i.e., the first imaging unit 202a and the second imaging unit 202b (two sets of the X-ray irradiation unit and the X-ray detection unit, i.e., the first X-ray irradiation unit 221a and the second X-ray irradiation unit 221b, and the first X-ray detection unit 222a and the second X-ray detection unit 222b).

That is, the X-ray imaging apparatus 200 according to the second embodiment is configured such that two kinds of X-ray imaging can be performed at two irradiation positions R separated from each other by two different imaging units, i.e., the first imaging unit 202a and the second imaging unit 202b. Note that the same portions having the same configuration as in the above-described first embodiment are denoted by the same reference numerals, and the descriptions thereof will be omitted.

Configuration of X-Ray Imaging Apparatus By Second Embodiment

Figure 10:
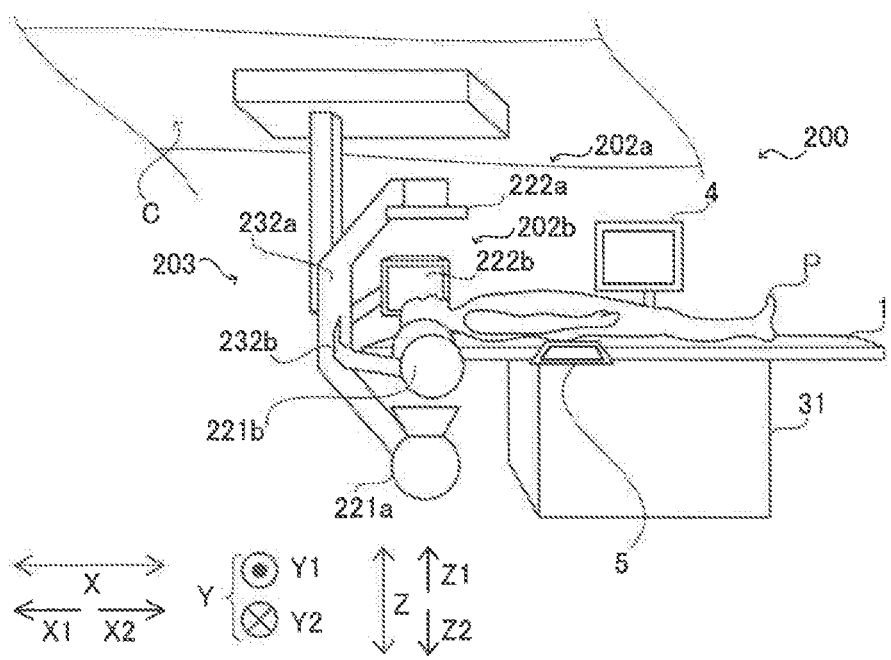
FIG. 10 is a front view for explaining an entire configuration of an X-ray imaging apparatus according to a second embodiment.
Figure 11:
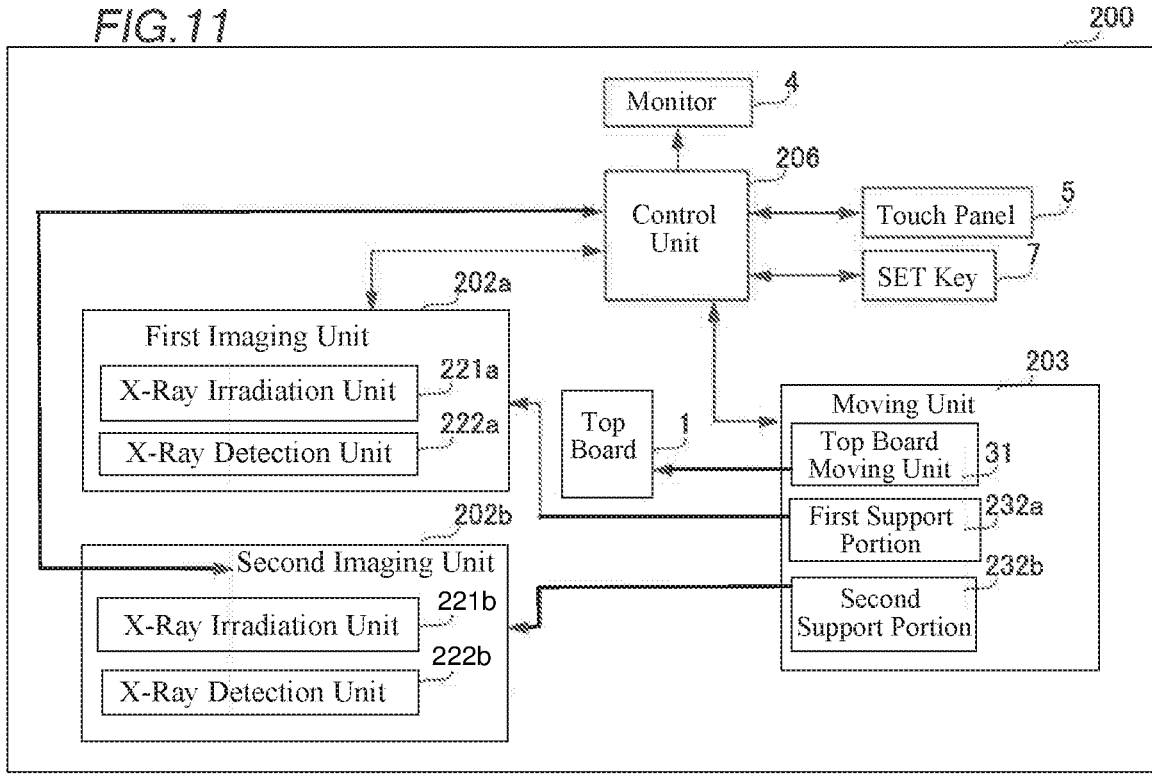
FIG. 11 is a block diagram showing an entire configuration of an X-ray imaging apparatus according to a second embodiment.

As shown in FIG. 10 and FIG. 11, the X-ray imaging apparatus 200 according to the second embodiment of the present invention is provided with a first imaging unit 202a, a second imaging unit 202b, a moving unit 203, and a control unit 206.

The first imaging unit 202a includes a first X-ray irradiation unit 221a for irradiating a subject P with X-rays and a first X-ray detection unit 222a for detecting the X-rays emitted from the first X-ray irradiation unit 221a. The first X-ray irradiation unit 221a and the first X-ray detection unit 222a are arranged so as to face each other with a top board 1 on which a subject P is placed interposed therebetween.

The second imaging unit 202b is provided separately from the first imaging unit 202a and includes a second X-ray irradiation unit 221b for irradiating the subject P with X-rays, and a second X-ray detection unit 222b for detecting the X-rays emitted from the second X-ray irradiation unit 221b. The second X-ray irradiation unit 221b and the second X-ray detection unit 222b are arranged so as to face each other with the top board 1 on which the subject P is placed interposed therebetween.

The moving unit 203 includes a first support portion 232a and the second support portion 232b. The first X-ray irradiation unit 221a and the first X-ray detection unit 222a are movably supported by the first support portion 232a, and the second X-ray irradiation unit 221b and the second X-ray detection unit 222b are movably supported by the second support portion 232b. In addition, the moving unit 203 is configured to change the first irradiation position Ra which is a position of the subject P to be irradiated with X-rays by the first imaging unit 202a and change the second irradiation position Rb which is a position of the subject P to be irradiated with X-rays by the second imaging unit 202b.

The control unit 206 performs X-ray imaging at two irradiation positions separated from each other, i.e., the first irradiation position Ra and the second irradiation position Rb by controlling the operation of the moving unit 203 and controlling two different imaging units, i.e., the first imaging unit 202a and the second imaging unit 202b to acquire two X-ray images A different from each other. In addition, based on the X-ray imaging by the two imaging units different from each other, i.e., the first imaging unit 202a and the second imaging unit 202b, the control unit displays two two-dimensional virtual plane images V different from each other side by side on the monitor 4.

The control unit 206 is configured to generate a two-dimensional virtual plane image V such that the virtual plane and the top board 1 in the two-dimensional virtual plane image V displayed on the monitor 4 are oriented in a direction parallel to each other or in a direction perpendicular to each other, and display the generated two-dimensional virtual plane image V on the monitor 4. For example, as shown in FIG. 12A and FIG. 12B, when performing X-ray imaging on the head of the subject P, the control unit 206 is configured to generate a first image V30a for a head in which the virtual plane and the top board 1 are oriented in a direction in parallel with each other and a second image V30b for a head in which the virtual plane and the top board 1 are oriented in a direction perpendicular with each other and display them on the top board 1.

Figure 12A:
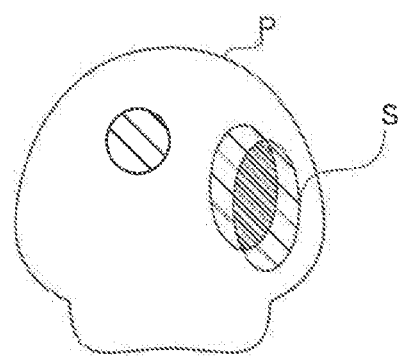
FIG. 12A is a diagram for explaining X-ray irradiation from two directions on a head of a subject according to a second embodiment and is a diagram showing X-ray irradiation from the back of the head.
Figure 12B:
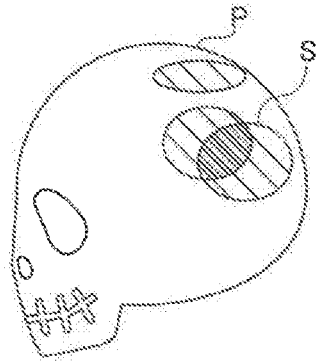
FIG. 12B is a diagram for explaining X-ray irradiation from two directions on a head of a subject according to a second embodiment and is a diagram showing X-ray irradiation from the side of the head.

Note that FIG. 12A and FIG. 12B schematically show the distribution S of the skin dose in the head of the subject P. FIG. 12A shows the X-ray imaging and the distribution of the skin dose by the first imaging unit 202a, and FIG. 12B shows the X-ray imaging and the distribution of the skin dose by the second imaging unit 202b.

As shown in FIG. 13A and FIG. 13B, the first image V30a for a head is a two-dimensional image in which the first irradiation position image V1a indicating the current first irradiation position R1a, the first skin dose image V2a indicating the skin dose for each of the first irradiation positions Ra, the first reference point Ka indicating the first reference position for the X-ray imaging by the first imaging unit 202a, and the scale image V3a indicating the angle with respect to the first reference position are superimposed on the virtual plane based on the X-ray imaging by the first imaging unit 202a. Further, the second image V30b for a head is a two-dimensional image in which the second irradiation position image V1b indicating the current second irradiation position R1b, the second skin dose image V2d indicating the skin dose for each of the second irradiation positions Rb, the second reference point Kb indicating the second reference position for the X-ray imaging by the second imaging unit 202b, and the scale image V3a indicating the angle with respect to the second reference position are superimposed on the virtual plane based on the X-ray imaging by the second imaging unit 202b. Note that the rest of the configuration of the second embodiment is the same as that of the first embodiment.

Effects of Second Embodiment

In this second embodiment, the following effects can be obtained.

In the second embodiment, as described above, the control unit 206 is configured to generate the two-dimensional virtual plane image V such that the virtual plane and the top board 1 in the two-dimensional virtual plane image V displayed on the monitor 4 (first display unit) are oriented in a direction parallel to each other or perpendicular to each other, and display the two-dimensional virtual plane image V on the monitor 4.

By configuring as described above, even in cases where the region of the subject P to be imaged is a head, by configuring the two-dimensional virtual plane in two planes perpendicular to each other, it is possible to generate the two-dimensional virtual plane so that the body surface of the subject P and the two-dimensional virtual plane are oriented in a direction in parallel to each other. As a result, the display of the skin dose on the two-dimensional virtual plane becomes a display viewed from substantially the same direction as the skin dose on the body surface of the subject P. Therefore, the skin dose of the subject P can be more easily recognized by checking the skin dose displayed on the two-dimensional virtual plane image V.

Further, in the second embodiment, as described above, when performing X-ray imaging of a head of a subject P, the control unit 206 is configured to generate the first image V30a for a head oriented in a direction in parallel to the top board 1 and the second image V30b for a head oriented in a direction perpendicular to the top board 1 and display them on the monitor 4 (first display unit).

By configuring as described above, when performing X-ray imaging of a head, the first image V30a for a head can indicate the skin dose of the back of the head, and the second image V30b for a head can indicate the skin dose of the side of the head. As a result, the skin dose of the entire head can be displayed more accurately, so that the position having a high skin dose in the entire head can be easily recognized and the X-rays can be emitted while avoiding the position having a high skin dose even when performing the treatment of the head.

The other effects of the second embodiment are the same as those of the above-described first embodiment.

Third Embodiment

Figure 15A:
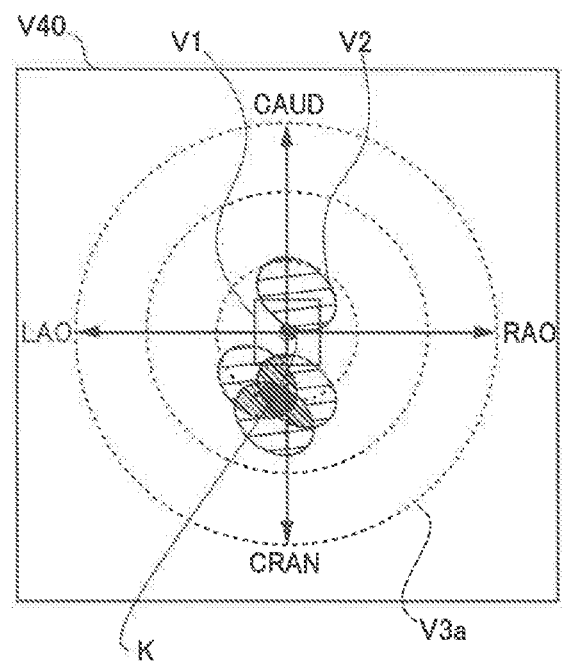
FIG. 15A is a diagram for explaining a two-dimensional virtual plane image according to a third embodiment and shows a state before changing an irradiation position.
Figure 15B:
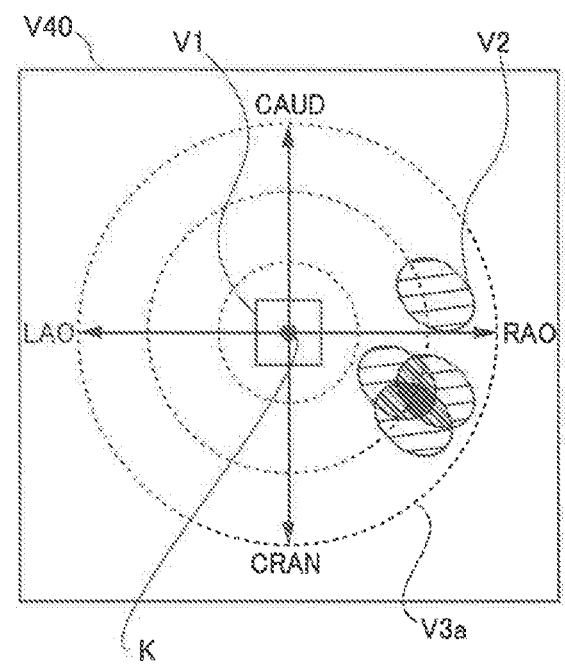
FIG. 15B is a diagram for explaining a two-dimensional virtual plane image according to the third embodiment and shows after the irradiation position is changed.

Referring to FIG. 14, FIG. 15A, and FIG. 15B, the configuration of the X-ray imaging apparatus 300 according to a third embodiment will be described. Unlike the first and second embodiments configured such that the image indicating the irradiation position R is superimposed on the two-dimensional virtual plane so that at least one of the distance and the angle with respect to the reference position can be visually distinguished and display it, in this third embodiment, it is configured such that the reference position and the irradiation position R match with each other and are superimposed on a two-dimensional virtual plane. Note that the same configuration portions as those of the above-described first and second embodiments are denoted by the same reference numerals, and the descriptions thereof will be omitted.

Configuration of X-Ray Imaging Apparatus By Third Embodiment

As shown in FIG. 14, the X-ray imaging apparatus 300 according to a third embodiment of the present invention is provided with a control unit 306.

The control unit 306 is configured to display the reference position (the reference point K, or the first reference point Ka and the second reference point Kb) and the current irradiation position R1 in the scale image V3 in a matched manner, in the two-dimensional virtual plane image V. For example, as shown in FIG. 15A and FIG. 15B, in the two-dimensional virtual plane image V40, the distribution of the skin dose may be displayed with the reference point K (the first reference point Ka and the second reference point Kb) which is the center position of the scale image V3a indicating the angle with respect to the reference position set as the current irradiation position R1. For example, as shown in FIG. 15A, when the irradiation position R is moved in the LAO-direction from the state displayed, it is displaced as shown in FIG. 15B. Note that the rest of the configuration of the third embodiment is the same as that of the first and second embodiments.

Effects of Third Embodiment

In this third embodiment, the following effects can be obtained.

In the third embodiment, as described above, the control unit 306 is configured to show the reference position (the reference point K, or the first reference point Ka and the second reference point Kb) in the scale image V3a and the current irradiation position R1 in a matched state in the two-dimensional virtual plane image V40.

As a result, even when the irradiation position R is changed, the position which is the reference of the two-dimensional virtual plane is displayed so as to show the irradiation position R at all times. By configuring as described above, the relative positional relationship between the current irradiation position R and the distribution of the skin dose can be easily recognized even when the irradiation position R is changed. As a result, it is possible to easily emit X-rays while avoiding the current irradiation position R and the position having a high skin dose.

The other effects of the third embodiment are the same as those of the above-described first and second embodiments.

[Modification]

It should be noted that the embodiments disclosed herein are to be considered in all respects as illustrative and not restrictive. The scope of the present invention is indicated by claims rather than by the embodiments described above, and includes all modifications within the meanings and scopes equivalent to claims.

(First Modification)

For example, in the above-described first to third embodiments, an example is shown in which the control unit 6 (the control unit 206 or the control unit 306) is configured to display on the monitor 4 the two-dimensional virtual plane image V including the skin dose image V2 which is an image indicating the skin dose so as to visually indicate the magnitude of the skin dose, the reference point K indicating the reference position, the scale image V3a or V3b in which the circular scale centered on the reference point K is provided in a circular shape centered on the control unit 306 so as to indicate at least one of the distance and the angle with respect to the reference position, and the irradiation position image V1 which is an image indicating the current irradiation position R1, but the present invention is not limited thereto. For example, as in the X-ray imaging apparatus of the first modification shown in FIG. 16, a two-dimensional virtual plane image V50 may be configured by not using the scale image V3a or V3b having a circular scale, but using a scale image V3c which is an angle map in which the skin dose in a plurality of irradiation positions R is displayed in the form of a grid for each angle of the imaging unit 2 or the first imaging unit 202a and the second imaging unit 202b.

Figure 16:
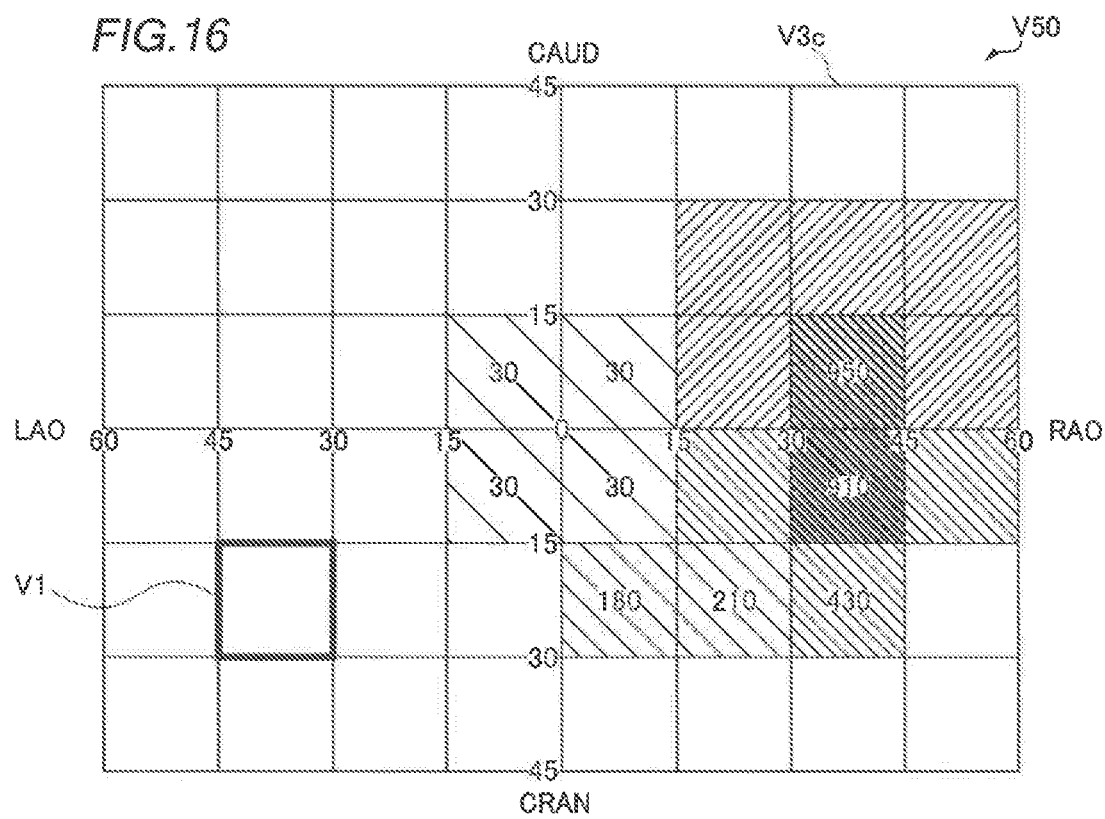
FIG. 16 is a diagram for explaining a scale image which is an angle map displayed in a grid pattern for each angle of an imaging unit of an X-ray imaging apparatus according to a first modification of the first to third embodiments.

Specifically, as shown in FIG. 16, the irradiation range is displayed in a grid pattern for each angle of the support portion 32, the skin dose in each of the irradiation ranges is calculated, and the highest skin dose among them is acquired as a peak skin dose value. When an operator determines the irradiation position R, the angular position in each of the irradiation positions R and the peak skin value in each of the irradiation positions R are arranged on the form of a grid so as to visually recognize them, and the irradiation position R may be determined based on the distribution of the skin dose.

(Second Modification)

Figure 17:
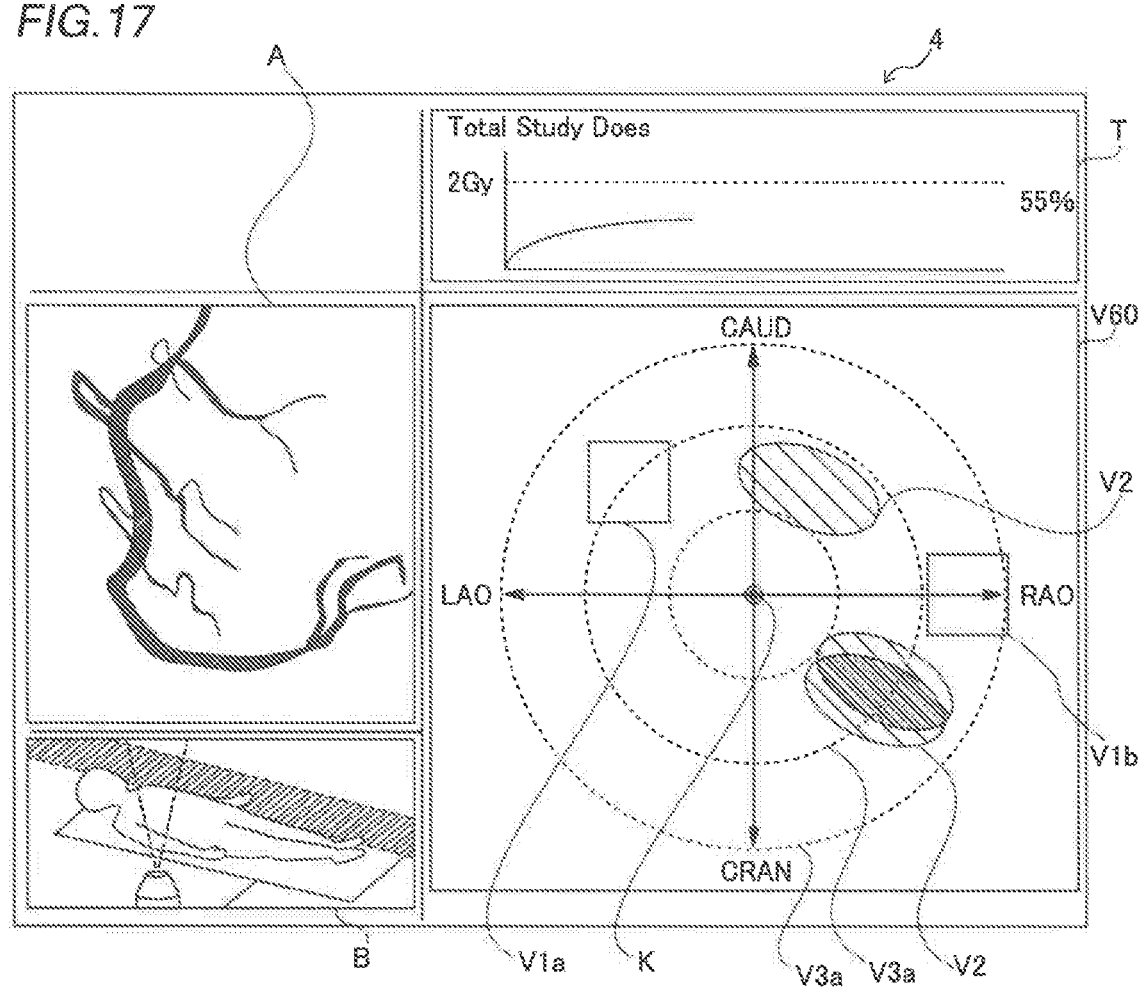
FIG. 17 is a diagram for explaining a display of two irradiation positions by two imaging units on a two-dimensional virtual plane of an X-ray imaging apparatus according to a second modification of the first to third embodiments.

Note that in the above-described first to third embodiments, an example is shown in which a single irradiation position image V1 is displayed on the two-dimensional virtual plane image V, but the present invention is not limited to this. For example, when a plurality of imaging units different from each other is provided, it may be configured that a plurality of irradiation position images V1 different from each other is displayed on the two-dimensional virtual plane image V. Specifically, like in the X-ray imaging apparatus of the second modification shown in FIG. 17, in cases where when the first imaging unit 202a and the second imaging unit 202b which are two imaging units different from each other are provided, the first irradiation position image V1a and the second irradiation position image V1b which are two irradiation position images different from each other may be displayed on the two-dimensional virtual plane image V60.

(Other Modification)

Further, in the above-described first to third embodiments, the control unit 6 (the control unit 206 or the control unit 306) is configured to perform control for displaying on the monitor 4 the two-dimensional virtual plane image V in which the skin dose image V2 which is an image indicating the skin dose for each of the irradiation positions R, the scale image V3 which is formed two-dimensionally so as to include substantially the entire region of the movable range of the moving unit 3 and indicates at least one of the distance and the angle with respect to the reference position, and the irradiation position image V1 which is an image indicating the current irradiation position R1 are superimposed on a virtual plane, but the present invention is not limited thereto. For example, the scale image V3 may be configured to indicate a part of the movable range of the moving unit 3.

Further, in the above-described first to third embodiments, an example is shown in which the control unit 6 (the control unit 206 or the control unit 306) is configured to display the skin dose total amount image T which is an image indicating the total amount of the skin dose of the subject P during the operation and the two-dimensional virtual plane image V on the monitor 4 side by side, but the present invention is not limited thereto. For example, it may be configured such that a display unit is newly provided separately from the monitor 4 and the skin dose total amount image T is displayed on the newly provided display unit. Alternatively, a skin dose total amount image T may be displayed on the touch panel 5.

Alternatively, it may be configured such that the total amount of the skin dose can be identified, without displaying the skin dose total amount image T. For example, it may be configured such that a notification unit is newly provided to issue a warning by voice or light when the total amount of the skin dose exceeds a predetermined threshold.

Further, in the above-described first to third embodiments, an example is shown in which it is configured such that the touch panel 5 for accepting an operation for determining the irradiation position R to perform X-ray imaging from among the plurality of irradiation positions R is further provided and that the control unit 6 makes the touch panel 5 to display on the touch panel 5 the display that the irradiation position R is an irradiation position Rr recommended for performing the X-ray imaging among the plurality of irradiation positions R in a visually discriminable manner based on the irradiation position Rr and the skin dose, but the present invention is not limited thereto. For example, an operation unit for accepting an operation and a display unit for displaying a display related to the irradiation position R may be provided separately. Further, the display of the recommended irradiation position Rr may be displayed on the monitor 4.

In the above-described first to third embodiments, an example is shown in which the control unit 6 (the control unit 206 or the control unit 306) is configured to display on the touch panel 5 an image indicating the irradiation position R among the irradiation positions R in which the skin dose exceeds a predetermined threshold as a non-recommended irradiation position Rn in a visually recognizable matter, but the present invention is not limited thereto. For example, it may be configured to be audibly recognizable rather than visually discriminable manner. That is, in the touch panel 5, when determining the irradiation position R, if it is attempted to determine the irradiation position R in which the skin dose exceeds a predetermined threshold, an alarm may be issued by voice. Further, as for the irradiation position R exceeding a predetermined threshold, it may be configured such that the operator cannot be selected by, for example, not displaying the irradiation position R exceeding the predetermined threshold on the touch panel 5.

In the above-described first to third embodiments, an example is shown in which the control unit 6 (the control unit 206 or the control unit 306) is configured to display the position information image D which is the information corresponding to each of the plurality of irradiation positions R on the touch panel 5 based on the irradiation position R and the skin dose, and determine at which irradiation position R among the plurality of irradiation positions R the X-ray imaging is to be performed the based on the input operation with respect to the touch panel 5, but the present invention is not limited to this. For example, it may be configured such that the irradiation position R is determined based on the distribution of the skin dose for each of the irradiation positions R displayed on the monitor 4 without displaying the position information image D.

In the above-described first to third embodiments, an example is shown in which the control unit 6 (the control unit 206 or the control unit 306) is configured to display on monitor 4 the two-dimensional virtual plane image V in which the image V1$d$ indicating the determined irradiation position Rd is displayed at the position corresponding to the determined irradiation position Rd on the virtual plane when it is determined at which irradiation position R the X-ray imaging is to be performed so that the position corresponding to the determined irradiation position Rd can be visually recognized, but the present invention is not limited thereto.

For example, it may be configured such that before determining at which irradiation position R the X-ray imaging is to be performed, the irradiation position Rr recommended to perform X-ray imaging is displayed on the monitor 4 so as to be visually recognizable, and the irradiation position R to perform X-ray imaging may be determined from among them.

Further, in the above-described first to third embodiments, an example is shown in which the control unit 6 (the control unit 206 or the control unit 306) is configured to display the plurality of position information images D on the touch panel 5 as a list and display on the touch panel 5 and to display on the touch panel 5 the current position information image D1 indicating the information on the current irradiation position R1 among the plurality of position information images D displayed as a list, the recommended position information image Dr indicating the information on the recommended irradiation position Rr, and the non-recommended position information image D indicating the information on the non-recommended irradiation position Dn in a visually discriminable manner, but the present invention is not limited to this. For example, it may be configured such that a list of position information images D is displayed on a display device provided separately from the touch panel 5. Further, it may be configured such that rather than displaying a plurality of position information images D as a list, the plurality of position information images is displayed in a pull-down format.

In the above-described second embodiment, an example is shown in which the control unit 206 is configured to generate the first image V30$a$ for a head and the second image V30$b$ for a head, which are two-dimensional virtual plane images V, so that the virtual plane and the top board 1 are oriented in parallel to each other or perpendicular to each other, and display them on the monitor 4, but the present invention is not limited to this. For example, it may be configured such that the virtual plane in the two-dimensional virtual plane image V is oriented in a direction that differs from the direction along the top board 1. Further, it may be configured such that the virtual plane in the two-dimensional virtual plane image V is oriented in a direction that differs from the direction along the direction perpendicular to the top board 1.

Further, in the above-described first to third embodiments, an example is shown in which when performing X-ray imaging on the heart of the subject P or the leg of subject P, the control unit 6 (the control unit 206 or the control unit 306) is configured to generate the image V10 for a heart and the image V20 for a leg so that the virtual plane and the top board 1 are oriented in parallel to each other and display them on the monitor 4 and when performing X-ray imaging of the heart of the subject P, but the present invention is not limited to this. For example, even in cases where X-ray imaging is performed for a heart and a leg, it may be configured to generate two kinds of two-dimensional virtual plane images V, i.e., the two-dimensional virtual plane image V including the virtual plane parallel to the top board 1 and the two-dimensional virtual plane image V including the virtual plane perpendicular to the top board 1.

Further, in the above-described second embodiment, an example is shown in which X-ray imaging is performed on the head of the subject P by using two different imaging units, i.e., the first imaging unit 202$a$ and the second imaging unit 202$b$, but the present invention is not limited to this. For example, when performing X-ray imaging on a heart of a subject P, it may be configured to use two imaging units that differ from each other, i.e., the first imaging unit 202a and the second imaging unit 202b.

Further, in the above-described first and third embodiments, an example is shown in which the control unit 6 (the control unit 206 or the control unit 306) is configured to display the X-ray image A captured by the imaging unit 2, or the first imaging unit 202a and the second imaging unit 202b, and the two-dimensional virtual plane image V on the monitor 4 side by side, but the present invention is not limited to this. For example, it may be configured such that the X-ray image A may be displayed on a new display device provided separately from the monitor 4.

Further, in the above-described third embodiment, an example is shown in which the control unit 306 is configured to display the reference position (the reference point K, or the first reference point Ka and the second reference point Kb) and the current irradiation position R1 in the scale image V3a in the two-dimensional virtual plane image V40 in a matched manner, but the present invention is not limited to this. For example, it may be configured such that the irradiation position image V1 which is an image indicating the current irradiation position R1 is not displayed on the two-dimensional virtual plane image V40. That is, it may be configured such that the image indicating the current irradiation position R1 is not displayed and the reference position of the scale image V3a is set as a position indicating the current irradiation position R1.

Further, in the above-described first to third embodiments, an example is shown in which during which the SET key 7 is being pressed by the operator, the control unit 6 (the control unit 206 or the control unit 306) is configured to control the moving units 3 and 203 so that the imaging unit 2 or the first imaging unit 202a and the second imaging unit 202b are moved to the position for emitting X-rays to the determined irradiation position Rd, but the present invention is not limited thereto. For example, it may be configured such that when the irradiation position R for performing X-ray imaging is determined by operating the touch panel 5, the imaging unit 2, or the first imaging unit 202a and the second imaging unit 202b are started to move.

Further, in the above-described first to third embodiments, an example is shown in which the irradiation position image V1 which is an image indicating the current irradiation position R1 is indicated by a rectangle, but the present invention is not limited to this. For example, it may be configured such that the irradiation position image V1 is indicated by an elliptical.

Further, in the above-described first to third embodiments, an example is shown in which the scale image V3 is indicated by the scale image V3a indicating the angle with respect to the reference position and the scale image V3b indicating the distance with respect to the reference position, but the present invention is not limited to this. It may be configured such that the scale image V3 is indicated by the scale image V3a indicating the angle and the distance with respect to the reference position by, for example, displaying the distance with respect to the reference position.

Further, in the above-described first to third embodiments, for the sake of convenience of explanation, an example is shown in which the explanation has been made using the flow-driven type flow chart in which the control processing of the control unit 6, the control unit 206, and the control unit 306 is performed in order along the processing flow, but the present invention is not limited to this. In the present invention, the control processing of the control unit 6, the control unit 206, and the control unit 306 may be performed by event-driven processing that executes processing on an event-by-event basis. In this case, the processing may be performed in a complete event-driven type or in combination of an event-driven and a flow-driven.

[Aspects]

It will be understood by those skilled in the art that the above-described exemplary embodiments are concrete examples of the following aspects.

(Item 1)

An X-ray imaging apparatus comprising:
a top board configured to place a subject thereon;
an imaging unit provided with an X-ray irradiation unit including an X-ray source for emitting X-rays to a subject, and an X-ray detection unit for detecting the X-rays emitted from the X-ray irradiation unit;
a moving unit configured to change an irradiation position which is a position of the subject to be irradiated with the X-rays by moving at least one of the imaging unit and the top board to irradiate the subject with the X-ray; and
a control unit configured to perform control for displaying on a first display unit a two-dimensional virtual plane image which is a two-dimensional image in which an image indicating a skin dose for each of a plurality of irradiation positions and a scale image indicating at least one of a distance and an angle with respect to a reference position are superimposed on a virtual plane.

(Item 2)

The X-ray imaging apparatus as recited in the above-described Item 1, wherein the control unit is configured to perform control for displaying on the first display unit the two-dimensional virtual plane image in which the image indicating the skin dose for each of the plurality of irradiation positions, the scale image formed two-dimensionally so as to include substantially an entire region of a movable range of the moving unit and configured to indicate at least one of the distance and the angle with respect to the reference position, and an image indicating a current irradiation position are superimposed on the virtual plane.

(Item 3)

The X-ray imaging apparatus as recited in the above-described Item 2, wherein the control unit is configured to display on the first display unit the two-dimensional virtual plane image including the image indicating the skin dose so as to visually indicate a magnitude of the skin dose, a reference point indicating the reference position, the scale image provided with a circular scale centered on the reference point so as to indicate at least one of the distance and the angle with respect to the reference position, and the image indicating the current irradiation position.

(Item 4)

The X-ray imaging apparatus as recited in any one of the above-described Items 1 to 3,
wherein the control unit is configured to display an image indicating a total amount of the skin dose of the subject during treatment and the two-dimensional virtual plane image on the first display unit side by side.

(Item 5)

The X-ray imaging apparatus as recited in any one of the above-described Items 1 to 4, further comprising:
an operation unit configured to accept an operation for determining the irradiation position at which X-ray imaging is to be performed from the plurality of irradiation positions,
wherein the operation unit includes a second display unit for displaying a display relating to the irradiation position, and
wherein the control unit is configured to display on the second display unit a display indicating that the irradiation position is the recommended irradiation position for performing the X-ray imaging from among the plurality of irradiation positions based on the irradiation position and the skin dose in a visually discriminable manner, (Item 6)

The X-ray imaging apparatus as recited in the above-described Item 5, wherein the control unit is configured to display on the second display unit of the operation unit an image indicating the irradiation position at which the skin dose exceeds a predetermined threshold among the plurality of irradiation positions in a visually discriminable manner as the irradiation position that is not recommended.

(Item 7)

The X-ray imaging apparatus as recited in the above-described Item 5 or 6, wherein the control unit is configured to display a position information image which is information corresponding to each of the plurality of irradiation positions on the second display unit of the operation unit based on the irradiation position and the skin dose and determine at which irradiation position the X-ray imaging is to be performed among the plurality of irradiation positions based on an input operation on the operation unit.

(Item 8)

The X-ray imaging apparatus as recited in the above-described Item 7, wherein the control unit is configured to display on the first display unit the two-dimensional virtual plane image in which an image indicating the determined irradiation position is displayed at a position corresponding to the determined irradiation position on the virtual plane such that the position corresponding to the determined irradiation position is visually discriminable when it is determined at which irradiation position the X-ray imaging is to be performed.

(Item 9)

The X-ray imaging apparatus as recited in the above-described Item 7 or 8, wherein the control unit is configured to display on the second display unit of the operation unit the plurality of position information images as a list and display on the second display unit of the operation unit an image indicating information relating to a current irradiation position among the plurality of position information images displayed as a list, an image indicating information relating to the recommended irradiation position, and an image indicating information relating to the non-recommended irradiation position in a visually distinguishable manner.

(Item 10)

The X-ray imaging apparatus as recited in any one of the above-described Items 1 to 9, wherein the control unit is configured to generate the two-dimensional virtual plane image such that the virtual plane and the top board in the two-dimensional virtual plane image displayed on the first display unit are oriented in a direction parallel to each other or a direction perpendicular to each other and display the two-dimensional virtual plane image on the first display unit.

(Item 11)

The X-ray imaging apparatus as recited in the above-described Item 10, wherein when performing the X-ray imaging of a heart and a leg of a subject, the control unit generates an image for a heart and a leg so that the virtual plane and the top board are oriented in a direction parallel to each other and displays the image for a heart and a leg on the first display unit, and wherein when performing the X-ray imaging of a head of a subject, it is configured such that a first image for a head oriented in a direction parallel to the top board and a second image for a head oriented in a direction perpendicular to to the top board are generated and displayed on the first display unit.

(Item 12)

The X-ray imaging apparatus as recited in the any one of above-described Items 1 to 11, wherein the control unit is configured to display the image captured by the imaging unit and the two-dimensional virtual plane image side by side on the first display unit.

(Item 13)

The X-ray imaging apparatus as recited in any one of the above-described Items 1 to 12, wherein the control unit is configured to display the reference position and the current irradiation position in the scale image so as to match with each other in the two-dimensional virtual plane image.

The invention claimed is:

1. An X-ray imaging apparatus comprising:
a top board configured to place a subject thereon;
an imaging unit provided with an X-ray irradiation unit including an X-ray source for emitting X-rays to a subject, and an X-ray detection unit for detecting the X-rays emitted from the X-ray irradiation unit;
a moving unit configured to change an irradiation position which is a position of the subject to be irradiated with the X-rays by moving at least one of the imaging unit and the top board to irradiate the subject with the X-ray; and
a control unit configured to perform control for displaying on a first display unit a two-dimensional virtual plane image which is a two-dimensional image in which an image indicating a skin dose for each of a plurality of irradiation positions and a scale image indicating at least one of a distance and an angle with respect to a reference position are superimposed on a virtual plane.

2. The X-ray imaging apparatus as recited in claim 1,
wherein the control unit is configured to perform control for displaying on the first display unit the two-dimensional virtual plane image in which the image indicating the skin dose for each of the plurality of irradiation positions, the scale image formed two-dimensionally so as to include substantially an entire region of a movable range of the moving unit and configured to indicate at least one of the distance and the angle with respect to the reference position, and an image indicating a current irradiation position are superimposed on the virtual plane.

3. The X-ray imaging apparatus as recited in claim 2,
wherein the control unit is configured to display on the first display unit the two-dimensional virtual plane image including the image indicating the skin dose so as to visually indicate a magnitude of the skin dose, a reference point indicating the reference position, the scale image provided with a circular scale centered on the reference point so as to indicate at least one of the distance and the angle with respect to the reference position, and the image indicating the current irradiation position.

4. The X-ray imaging apparatus as recited in claim 1,
wherein the control unit is configured to display an image indicating a total amount of the skin dose of the subject during treatment and the two-dimensional virtual plane image on the first display unit side by side.

5. The X-ray imaging apparatus as recited in claim 1, further comprising:
an operation unit configured to accept an operation for determining the irradiation position at which X-ray imaging is to be performed from the plurality of irradiation positions,
wherein the operation unit includes a second display unit for displaying a display relating to the irradiation position, and
wherein the control unit is configured to display on the second display unit a display indicating that the irradiation position is the recommended irradiation position for performing the X-ray imaging from among the plurality of irradiation positions based on the irradiation position and the skin dose in a visually discriminable manner.

6. The X-ray imaging apparatus as recited in claim 5, wherein the control unit is configured to display on the second display unit of the operation unit an image indicating the irradiation position at which the skin dose exceeds a predetermined threshold among the plurality of irradiation positions in a visually discriminable manner as the irradiation position that is not recommended.

7. The X-ray imaging apparatus as recited in claim 5, wherein the control unit is configured to display a position information image which is information corresponding to each of the plurality of irradiation positions on the second display unit of the operation unit based on the irradiation position and the skin dose and determine at which irradiation position the X-ray imaging is to be performed among the plurality of irradiation positions based on an input operation on the operation unit.

8. The X-ray imaging apparatus as recited in claim 7, wherein the control unit is configured to display on the first display unit the two-dimensional virtual plane image in which an image indicating the determined irradiation position is displayed at a position corresponding to the determined irradiation position on the virtual plane such that the position corresponding to the determined irradiation position is visually discriminable, when it is determined at which irradiation position the X-ray imaging is to be performed.

9. The X-ray imaging apparatus as recited in claim 7, wherein the control unit is configured to display on the second display unit of the operation unit the plurality of position information images as a list and display on the second display unit of the operation unit an image indicating information relating to a current irradiation position among the plurality of position information images displayed as a list, an image indicating information relating to the recommended irradiation position, and an image indicating information relating to the non-recommended irradiation position in a visually distinguishable manner.

10. The X-ray imaging apparatus as recited in claim 1, wherein the control unit is configured to generate the two-dimensional virtual plane image such that the virtual plane and the top board in the two-dimensional virtual plane image displayed on the first display unit are oriented in a direction parallel to each other or a direction perpendicular to each other and display the two-dimensional virtual plane image on the first display unit.

11. The X-ray imaging apparatus as recited in claim 10, wherein when performing the X-ray imaging of a heart and a leg of a subject, the control unit generates an image for a heart and a leg so that the virtual plane and the top board are oriented in a direction parallel to each other and displays the image for a heart and a leg on the first display unit, and
wherein when performing the X-ray imaging of a head of a subject, it is configured such that a first image for a head oriented in a direction parallel to the top board and a second image for a head oriented in a direction perpendicular to the top board are generated and displayed on the first display unit.

12. The X-ray imaging apparatus as recited in claim 1, wherein the control unit is configured to display the image captured by the imaging unit and the two-dimensional virtual plane image side by side on the first display unit.

13. The X-ray imaging apparatus as recited in claim 1, wherein the control unit is configured to display the reference position and the current irradiation position in the scale image so as to match with each other in the two-dimensional virtual plane image.

* * * * *